United States Patent
Siegler et al.

(10) Patent No.: US 10,463,434 B2
(45) Date of Patent: Nov. 5, 2019

(54) TRACKING MARKER SUPPORT STRUCTURE AND SURFACE REGISTRATION METHODS EMPLOYING THE SAME FOR PERFORMING NAVIGATED SURGICAL PROCEDURES

(71) Applicant: 7D SURGICAL INC., Toronto (CA)

(72) Inventors: Peter Siegler, Toronto (CA); Michael Leung, Markham (CA); Adrian Mariampillai, Toronto (CA); Beau Anthony Standish, Toronto (CA); Victor X. D. Yang, Toronto (CA)

(73) Assignee: 7D SURGICAL INC., Toronto, ON (CA)

( * ) Notice: Subject to any disclaimer, the term of this patent is extended or adjusted under 35 U.S.C. 154(b) by 309 days.

(21) Appl. No.: 15/513,862

(22) PCT Filed: Sep. 23, 2015

(86) PCT No.: PCT/CA2015/050939
§ 371 (c)(1),
(2) Date: Mar. 23, 2017

(87) PCT Pub. No.: WO2016/044934
PCT Pub. Date: Mar. 31, 2016

(65) Prior Publication Data
US 2017/0281283 A1    Oct. 5, 2017

Related U.S. Application Data

(60) Provisional application No. 62/054,784, filed on Sep. 24, 2014.

(51) Int. Cl.
*A61B 17/58* (2006.01)
*A61B 17/60* (2006.01)
(Continued)

(52) U.S. Cl.
CPC ............ *A61B 34/20* (2016.02); *A61B 5/1127* (2013.01); *A61B 5/6847* (2013.01); *A61B 17/28* (2013.01);
(Continued)

(58) Field of Classification Search
CPC combination set(s) only.
See application file for complete search history.

(56) References Cited

U.S. PATENT DOCUMENTS 6,021,343 A    2/2000   Foley et al.
6,167,145 A   12/2000   Foley et al.
(Continued)

FOREIGN PATENT DOCUMENTS

CN    101862220      10/2010
DE    102009034668   1/2011

OTHER PUBLICATIONS

International Search Report (PCT/CA2015/050939) dated Jan. 26, 2016.
Written Opinion PCT/CA2015/050939 dated Jan. 26, 2016.

*Primary Examiner* — Sameh R Boles
(74) *Attorney, Agent, or Firm* — Hill & Schumacher

(57) ABSTRACT

Devices and methods are provide for facilitating registration and calibration of surface imaging systems. Tracking marker support structures are described that include one or more fiducial reference markers, where the tracking marker support structures are configured to be removably and securely attached to a skeletal region of a patient. Methods are provided in which a tracking marker support structure is attached to a skeletal region in a pre-selected orientation, thereby establishing an intraoperative reference direction associated with the intraoperative position of the patient, which is employed for guiding the initial registration between intraoperatively acquired surface data and volumetric image data. In other example embodiments, the tracking
(Continued)

marker support structure may be employed for assessing the validity of a calibration transformation between a tracking system and a surface imaging system. Example methods are also provided to detect whether or not a tracking marker support structure has moved from its initial position during a procedure.

24 Claims, 43 Drawing Sheets

(51) Int. Cl.
*A61F 2/00* (2006.01)
*A61B 34/20* (2016.01)
*A61B 17/28* (2006.01)
*A61B 5/00* (2006.01)
*A61B 5/11* (2006.01)
*A61B 90/00* (2016.01)
*A61B 17/88* (2006.01)
*A61B 17/30* (2006.01)
*A61B 17/00* (2006.01)
*A61B 17/56* (2006.01)
*A61B 17/90* (2006.01)
*A61B 90/16* (2016.01)

(52) U.S. Cl.
CPC .......... *A61B 17/2833* (2013.01); *A61B 17/88* (2013.01); *A61B 90/37* (2016.02); *A61B 5/6878* (2013.01); *A61B 17/282* (2013.01); *A61B 17/2812* (2013.01); *A61B 17/8866* (2013.01); *A61B 90/16* (2016.02); *A61B 2017/00694* (2013.01); *A61B 2017/2837* (2013.01); *A61B 2017/303* (2013.01); *A61B 2017/564* (2013.01); *A61B 2017/90* (2013.01); *A61B 2034/207* (2016.02); *A61B 2034/2055* (2016.02); *A61B 2034/2057* (2016.02); *A61B 2090/364* (2016.02); *A61B 2090/371* (2016.02); *A61B 2090/373* (2016.02); *A61B 2090/3916* (2016.02); *A61B 2090/3983* (2016.02); *A61B 2090/3991* (2016.02); *A61B 2560/0233* (2013.01)

(56) References Cited

U.S. PATENT DOCUMENTS

| | | | |
|---|---|---|---|
| 6,223,067 B1 | 4/2001 | Vilsmeier et al. | |
| 6,226,548 B1 | 5/2001 | Foley et al. | |
| 6,241,735 B1 | 6/2001 | Marmulla | |
| 6,275,725 B1 | 8/2001 | Cosman | |
| 6,282,437 B1 | 8/2001 | Franck et al. | |
| 6,932,823 B2 | 8/2005 | Grimm et al. | |
| 7,079,885 B2 | 7/2006 | Marmulla et al. | |
| 7,107,091 B2 | 9/2006 | Jutras et al. | |
| 7,217,276 B2 | 5/2007 | Henderson et al. | |
| 7,970,174 B2 | 6/2011 | Goldbach | |
| 7,993,353 B2 | 8/2011 | Roβner et al. | |
| 8,068,648 B2 | 11/2011 | DiSilvestro et al. | |
| 8,165,366 B2 | 4/2012 | Haimerl et al. | |
| 8,165,659 B2 | 4/2012 | Sheffer et al. | |
| 8,180,429 B2 | 5/2012 | Sasso | |
| 8,238,631 B2 | 8/2012 | Harmann et al. | |
| 8,323,295 B2 | 12/2012 | Hüfner et al. | |
| 8,467,851 B2 | 6/2013 | Mire et al. | |
| 8,475,470 B2 | 7/2013 | von Jako | |
| 8,509,878 B2 | 8/2013 | Pfeifer et al. | |
| 8,535,329 B2 | 9/2013 | Sarin et al. | |
| 8,571,637 B2 | 10/2013 | Sheffer et al. | |
| 8,644,570 B2 | 2/2014 | Hartmann et al. | |
| 8,660,635 B2 | 2/2014 | Simon et al. | |
| 8,715,296 B2 | 5/2014 | Plaβky et al. | |
| 8,734,432 B2 | 5/2014 | Tuma et al. | |
| 2004/0082870 A1* | 4/2004 | Rudy | A61B 5/0402 600/509 |
| 2004/0176779 A1 | 9/2004 | Casutt et al. | |
| 2009/0024127 A1 | 1/2009 | Lechner et al. | |
| 2009/0062869 A1 | 3/2009 | Claverie et al. | |
| 2011/0134083 A1 | 6/2011 | Norieda | |
| 2014/0135658 A1 | 5/2014 | Hladio et al. | |

* cited by examiner

   
FIG. 9A     FIG. 9C     FIG. 9E     FIG. 9G
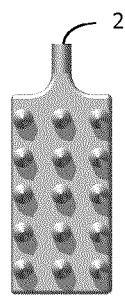 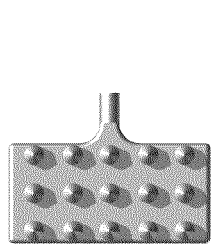 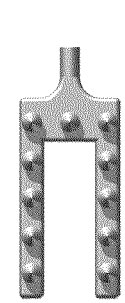 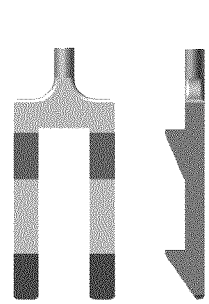
FIG. 9B     FIG. 9D     FIG. 9F     FIG. 9H    FIG. 9I
FIG. 9

| Feature | Lower Bound | Upper bound |
|---|---|---|
| Jaws | • Achieved gripping force should counteract torque from reference clamp and ensure stable attachment to object of interest | • Should minimize blocking line-of-sight target of surgeon and structural light system on surgical target |
| Angle between Members and Normal | • Marker attachment should be outside surgical cavity | • Reference frame should not obscure line of sight of surgeon and structure light imaging system to region of interest |
| Pivot Location | • Close to the clamping jaws in order to increase force translated from the surgeon's hand or tightening mechanism | • Spread of distal arms too big in order to held frame in a single hand and to avoid touching of incision borders<br>• No blocking line-of-sight of surgeon and structure light imaging system |
| Distance between Marker Attachment and Jaws | • Reference frame should not obscure line of sight of surgeon and structure light imaging system to region of interest<br>• No shadowing of other tracked tools to or from marker attachment | • Torque applied about gripping tip should not damage clamped structure<br>• Gripping force required to counteract torque of the frame should not break the object being clamped on<br>• Reference frame should be inside tracking and structural light imaging volumes |
| Height of Marker Attachment relative to Jaws | • No touching of any parts of the surgical cavity beside gripping area in order to avoid motion derived from sources other than the gripping point | • No blocking surgeon's movement or used instrumentation during surgery |
| Angle of Marker Attachment | | • Perpendicular to optical axis of tracking system |
| Handling | | • One handed activation<br>• Fast tightening mechanism (interlocking teeth/ratchet)<br>• Markers should not touch the surgeon hand in order to avoid covering by blood or other liquids which facilitates accurate tracking |
| Add | | • Surface features to facilitate structural light registration<br>• Characteristic structures like divots to verify tracking of other tools<br>• Matte surface properties to reduce chance of interference with tracking subsystem and saturation of structured light subsystem |

FIG. 16

| Feature | | Variable | Range |
|---|---|---|---|
| Dimensions of Jaws | 1520 | length (l) | 10-30 mm |
| | 1525 | width (w) | 5-20 mm |
| | | thickness | 3-6 mm |
| Angle between Members and Normal | 1530 | α | 20°-40° |
| Pivot Location | 1570 | d | 20-40 mm |
| Distance between Marker Attachment and Jaws | 1550 | D | 70-120 mm |
| Perpendicular Offset of Marker Attachment relative to Jaws | 1540 | H | 80-120 mm |
| Angle of Marker Attachment | 1560 | β | 70°-110° |

FIG. 18

| Feature | Variable | | Range |
|---|---|---|---|
| Dimensions of Jaws | 1670 | length (l) | 5-20 mm |
| | 1675 | width (w) | 5-8 mm |
| | | thickness | 2-5 mm |
| Angle between Members and Normal | 1680 | α | 20°-40° |
| Distance between Marker Attachment and Jaws | 1685 | D | 50-120 mm |
| Perpendicular Offset of Marker Attachment relative to Jaws | 1690 | H | 30-60 mm |
| Angle of Marker Attachment | 1695 | β | 70°-110° |

FIG. 19F

| Feature | Variable | | Range |
|---|---|---|---|
| Dimensions of Jaw | 2325 | length (l) | 10-20mm |
| | | Hook width (w) | 5-10 mm |
| | | thickness | 2-3 mm |
| Distance between Jaw and Hook | 2320 | d | 3 mm - 20 mm |
| Angle between Members and Normal | 2330 | α | 30°-60° |
| Distance between Marker Attachment and Jaws | 2350 | D | 70-150 mm |
| Perpendicular Offset of Marker Attachment relative to Jaws | 2340 | H | 30-70 mm |
| Angle of Marker Attachment | 2360 | β | 50°-130° |

FIG. 22F

TRACKING MARKER SUPPORT STRUCTURE AND SURFACE REGISTRATION METHODS EMPLOYING THE SAME FOR PERFORMING NAVIGATED SURGICAL PROCEDURES

CROSS-REFERENCE TO RELATED APPLICATION

This application is a National Phase application claiming the benefit of the international PCT Patent Application No. PCT/CA2015/050939, filed on Sep. 23, 2015, in English, which claims priority to U.S. Provisional Application No. 62/054,784, titled "TRACKING MARKER SUPPORT STRUCTURE AND SURFACE REGISTRATION METHODS EMPLOYING THE SAME FOR PERFORMING NAVIGATED SURGICAL PROCEDURES" and filed on Sep. 24, 2014, the entire contents of which are incorporated herein by reference.

BACKGROUND

Surgical guidance enables surgeons to localize the position of surgical instruments relative to the human body without having complete visual access during surgery. Surgical guidance is routinely used in surgeries that involve anatomical locations such as the spine, brain, hip or other organs.

In general, surgical guidance consists of two steps: The first step includes the acquisition of a three dimensional (3D) data set of a relevant anatomical region of the body. This step may involve single or multiple imaging modalities such as computed tomography (CT), magnetic resonance tomography (MRT), positron emission tomography (PET) and ultrasound (US). The 3D data set may be acquired before and/or during the surgical procedure. In the second step, the spatial position of the body and the spatial relation of the surgical instruments to the position of the anatomical region are tracked during the surgery. The spatial position of this anatomical region is then mapped to its 3D data set using specific image registration techniques. After registration, the spatial position of the surgical instruments as they are being used by the surgeon can be displayed relative to the previously acquired 3D data set of the anatomical region. Surgical guidance systems usually incorporate the use of a reference structure which is affixed to the patient in order to track patient motion and breathing so that tool tracking remains accurate during the procedure.

In some applications, optical-based systems are used for tracking spatial positions of tools and the reference frame during the surgery. These systems are based on two cameras that detect the positions of at least three markers attached to the tracked surgical instruments and require line-of-sight from the cameras to the markers (for example, mounted with LEDs, or mounted with reflective probes). This necessitates the careful positioning of the cameras and design of tracked instruments so that line-of-sight is maintained during a surgical procedure.

SUMMARY

Devices and methods are provided for facilitating registration and calibration of surface imaging systems. Tracking marker support structures are described that include one or more fiducial reference markers, where the tracking marker support structures are configured to be removably and securely attached to a skeletal region of a patient. Methods are provided in which a tracking marker support structure is attached to a skeletal region in a pre-selected orientation, thereby establishing an intraoperative reference direction associated with the intraoperative position of the patient, which is employed for guiding the initial registration between intraoperatively acquired surface data and volumetric image data. In other example embodiments, the tracking marker support structure may be employed for assessing the validity of a calibration transformation between a tracking system and a surface imaging system. Example methods are also provided to detect whether or not a tracking marker support structure has moved from its initial position during a procedure.

Accordingly, in a first aspect, there is provided a method of intraoperatively registering surface data with volumetric image data, the method comprising:

detecting, with a tracking system, signals associated with fiducial markers located on a tracking marker support structure, wherein the tracking marker support structure is removably attached to a skeletal feature of a subject in a pre-selected orientation relative to the skeletal feature;

processing the signals and employing the pre-selected orientation to determine an intraoperative reference direction associated with an intraoperative position and orientation of the subject;

intraoperatively acquiring the surface data from a surgical region of interest; and employing the intraoperative reference direction when registering the surface data to the volumetric image data.

In another aspect, there is provided a method of assessing the validity of a previously determined calibration transformation between a surface imaging system and a tracking system, the method comprising:

detecting, with the tracking system, signals associated with fiducial markers located on a tracking marker support structure, wherein the tracking marker support structure is removably attached to a patient, and acquiring surface data using the surface imaging system, wherein the surface data is obtained from a spatial region that includes at least a portion of the tracking marker support structure;

processing the signals to determine a position and orientation of the tracking marker support structure;

determining, based on the intraoperative position and orientation of the tracking marker support structure, and based on the previously determined calibration transformation between a reference frame of the surface imaging system and a reference frame of the tracking system, a spatial subregion, in the reference frame of the surface imaging system, that is associated with the tracking marker support structure;

segmenting the surface data within the spatial subregion to obtain a segmented surface associated with the tracking marker support structure;

registering the segmented surface to reference surface data characterizing the surface of the tracking marker support structure, thereby obtaining a spatially registered reference surface; and employing the spatially registered reference surface to assess the validity of the previously acquired calibration transformation.

In another aspect, there is provided a device for positioning fiducial markers relative to an exposed vertebrae, the device comprises:

a pair of forceps having a longitudinal axis associated therewith;

a pair of clamping jaws located near a distal region of the forceps, wherein the clamping jaws are configured to contact opposing sides of a spinous process when a force is applied to the forceps;

a locking mechanism operably connected to the forceps for removably maintaining the forceps in a clamped configuration; and a tracking frame having a proximal end connected to the forceps at a location remote from clamping jaws, wherein the tracking frame supports, near a distal region thereof, the fiducial markers;

wherein the forceps extend from the clamping jaws such that when the clamping jaws are clamped to the spinous process, the longitudinal axis associated with the forceps is angled relative to the Anterior-Posterior a normal direction that is associated with the subject, wherein the normal direction lies in the sagittal plane and is perpendicular to the Inferior-Superior direction of the spine, such that a skeletal region adjacent to the skeletal feature is unobstructed by the forceps, thereby permitting overhead surface data acquisition of the skeletal region; and wherein at least a portion of the tracking frame is angled relative the longitudinal axis of the forceps, such that contact is avoided between the fiducial markers and a user gripping the forceps.

In another aspect, there is provided a device for fixing fiducial markers relative to an exposed vertebrae, the device comprises:

a pair of forceps having a longitudinal axis;

a pair of clamping jaws located near a distal region of the forceps, wherein the clamping jaws are configured to contact opposing sides of a spinous process of the exposed vertebrae when a force is applied to the forceps;

a locking mechanism operably connected to the forceps for removably maintaining the forceps in a clamped configuration; and a tracking frame having a proximal end connected to the forceps at a location remote from clamping jaws, wherein the tracking frame supports, near a distal region thereof, the fiducial markers;

wherein the clamping jaws are characterized by a normal axis that is perpendicular to the Inferior-Superior direction of the spine when the clamping jaws are clamped to the spinous process;

wherein the longitudinal axis of the forceps is angled relative to the normal axis of the clamping jaws, and such that a skeletal region adjacent to the skeletal feature is unobstructed by the forceps; and wherein at least a portion of the tracking frame is angled relative the longitudinal axis of the forceps, such that contact is avoided between the fiducial markers and a user gripping the forceps.

In another aspect, there is provided a device for fixing fiducial markers relative to an exposed vertebrae, the device comprises:

a pair of forceps having a longitudinal axis;

a pair of clamping jaws located near a distal region of the forceps;

a tracking frame having a proximal end connected to the forceps at a location remote from clamping jaws, wherein the tracking frame supports, near a distal region thereof, the fiducial markers;

a locking mechanism operably connected to the forceps for removably maintaining the forceps in a clamped configuration;

wherein the clamping jaws are shaped to uniquely contact opposing sides of a skeletal feature, such that the fiducial markers are oriented in a pre-selected orientation relative to the skeletal feature.

In another aspect, there is provided a clamping device for clamping to a spinous process, the device comprises:

a pair of forceps having a longitudinal axis;

a pair of clamping jaws located near a distal region of the forceps;

a locking mechanism operably connected to the forceps for removably maintaining the forceps in a clamped configuration;

wherein each clamping jaw comprises a clamping surface having two co-planar outer flat surfaces and an inwardly directed surface connecting the two outer flat surfaces, such that the clamping jaws are configured for clamping to a wide range of spinous process geometries, and wherein the outer flat surfaces and the inwardly directed surface each comprise spikes.

In another aspect, there is provided a method of detecting a change in the position and orientation of a tracking marker support structure relative to a patient to which the tracking marker support structure is attached, the method comprising:

detecting, with a tracking system, signals associated with the fiducial markers located on the tracking marker support structure, and acquiring surface data from a surgical region of interest using a surface imaging system;

determining the current position and orientation of the tracking marker support structure based on the signals;

obtaining previously measured surface data from the surgical region of interest and an associated previously determined position and orientation of the tracking marker support structure;

registering the surface data with previously acquired surface data to obtain an intraoperative transformation;

comparing the intraoperative transformation to the shift between the current position and orientation of the tracking marker support structure and the previously determined position and orientation of the tracking marker support structure and determining a change in the position and orientation of the tracking marker support structure relative to the patient.

In another aspect, there is provided a method of segmenting surface data to remove surface artifacts associated with an instrument having fiducial markers attached thereto, the method comprising:

intraoperatively acquiring the surface data from a surgical region of interest using a surface imaging system;

detecting, with a tracking system, signals associated with the fiducial markers located on the instrument, processing the signals to determine an intraoperative position and orientation of the instrument;

employing the intraoperative position and orientation of the instrument, and employing a calibration transformation between a reference frame associated with the tracking system and a reference frame associated with the surface imaging system, to determine a suitable position and orientation of a cropping mask for removal of the surface artifacts associated with the instrument; and segmenting the surface data to remove the surface artifacts within the region associated with the cropping mask.

BRIEF DESCRIPTION OF DRAWINGS

Embodiments will now be described, by way of example only, with reference to the drawings, in which:

FIGS. 9A-I show different example implementations of clamping jaws employed by the gripping mechanism.

FIG. 16 itemizes the characteristic features, and associated design constraints, of an example tracking marker support structure.

FIG. 18 provides example values for the dimensions of the characteristic geometrical parameters identified in FIG. 17.

FIG. 19F provides example values for the dimensions of the characteristic geometrical parameters identified in FIG. 19E.

FIG. 22F provides example values for the dimensions of the characteristic geometrical parameters identified in FIG. 22D.

DETAILED DESCRIPTION

Figure 1A:
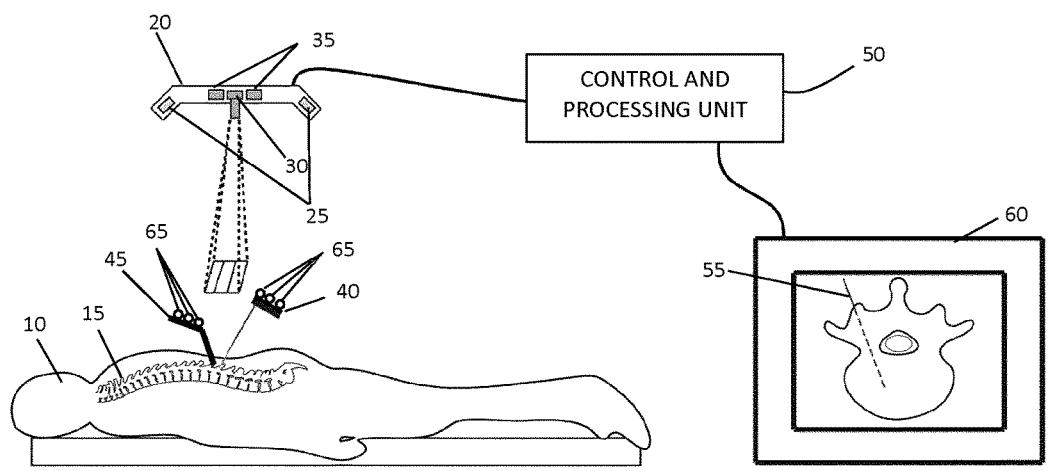
FIG. 1A shows a schematic of an example surgical guidance system that includes an overhead integrated tracking system that employs structured light surface detection for image registration and optical tracking of medical instruments and medical devices with marker attachments.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings.

As used herein, the term "position" refers to the location (e.g. x,y,z) of an object and its orientation (e.g. relative to one or more rotational axes) in three dimensions (3D) within a coordinate system.

As used herein, the term "tracking system" refers to a system that allows the detection of the position of an object in three dimensions. An example of a tracking system is an optical tracking system operating with visual or infrared light that may employ stereo cameras to detect the positions of passive optical markers (e.g. reflective spheres) and/or active optical markers (e.g. light emitting diodes (LEDs)). Other non-limiting examples of tracking systems include electromagnetic tracking systems and surface imaging tracking systems.

As used herein, the term "marker" refers to a locating indicator that may be affixed or otherwise connected to a flexible or rigid handheld implement, patient, subject, instrument, tool, or other component of a surgical system or surgical field, and which is detectable by a tracking system for use in determining a position. A marker may be active or passive, and may be detectable using an optical or electromagnetic detector. An example optical passive marker is a reflective sphere, or portion thereof, and an example active optical marker is an LED. Another example of a marker is a glyph, which may contain sufficient spatial and/or geometrical co-planar features for determining a three-dimensional position and orientation. For example, a glyph marker may include at least three corner features, where the three corner features define a plane.

As used herein, the term "surface imaging system" refers to a system that detects the topology of a 3D surface (e.g. acquires a set of surface data describing the surface topology) within a field of view. Examples of surface imaging techniques include structured light illumination, laser range finding, and photogrammetry.

As used herein, the term "calibration transformation" refers to a transformation that relates the coordinate system of a surface imaging system to that of a tracking system. The term "last calibration transformation" refers to the last valid or correct calibration transformation of the system. The last calibration can be determined either during the last service maintenance or by the system itself using a validation step.

As used herein, the term "tracking marker support structure" refers to a rigid structure including one or more fiducial or reference markers for intraoperative tracking, that configured to be securely attached to a subject (e.g. vertebra or the head), for example, to facilitate a registration process.

FIG. 1A shows an illustration of an example of a surgical guidance system for tracking the intraoperative position of a medical instrument relative to patient anatomy during a spinal surgery. Patient 10 is shown in the prone (face down) position, with spine 15 exposed. Although the present example system employs a combination of an optical tracking system and a structured light surface imaging system, it will be understood that other types of tracking systems (i.e. non-optical) may be employed, and that other types of surface imaging systems (i.e. other than employing structured light) may be employed.

The optical tracking subsystem is used to detect the position of medical instrument 40. In the example embodiment shown in FIG. 1, the optical tracking subsystem includes stereo cameras with integrated infrared lighting 25 and attachment of highly reflective markers 65 to medical instrument 40. Due to their high reflectivity to infrared light, markers 65 can be easily localized in each image of the two cameras 25. These image positions are used to calculate the 3D position of each marker 65 by geometrical triangulation. If at least three markers 65 are rigidly attached to medical instrument 40, it is possible to compute its position (the six degrees of freedom—6-DOF). It is to be understood that in some embodiments, less than three markers may be employed for position tracking. For example, a single marker may be provided for position tracking, provided that the single marker includes sufficient spatial structure and/or content. An example of such a single marker is a glyph including co-planar spatial features such as corner or edge features.

In the example illustrations provided herein, markers 65 for the optical tracking system are shown as reflective spheres, which are commonly used for passive optical tracking. However, any other type of markers, or marker attributes, can be used depending on the used tracking system such as, but not limited to LEDs, which do not require integration of additional lighting, reflective spheres, glyphs, varying marker color, varying marker size, varying marker shape.

The structured light imaging subsystem shown in the example embodiment is used to generate surface datasets. It includes at least one illumination device 30 and at least one camera 35. The illumination device(s) 30 project temporally and/or spatially modulated light onto the surface to be imaged, while the camera(s) 35 capture images of the illuminated surface. This active illumination enables robust and efficient identification of pixel correspondences between calibrated camera-projector (a projector may be thought of as an inverse camera) or calibrated camera-camera system. The correspondence (disparity) data can then be transformed into real-space coordinate data in the coordinate system of the calibrated camera(s) 35 and/or projector(s) 30 by geometrical triangulation. During surgery, the structured light imaging system is positioned such that 3D surface of the surgical site (e.g. the bony surfaces of the exposed spine 15) is acquired. The created virtual representation of the 3D surface is then registered to volumetric image data (e.g. CT, MRI, US, PET, etc.) by processing unit 50, using, for example, methods described in International Patent Application No. PCT/CA2011/050257. The volumetric image data may be pre-operatively acquired, but is not necessarily pre-operatively acquired. For example, in some applications, the volumetric image data may also be intra-operatively acquired.

Figure 1B:
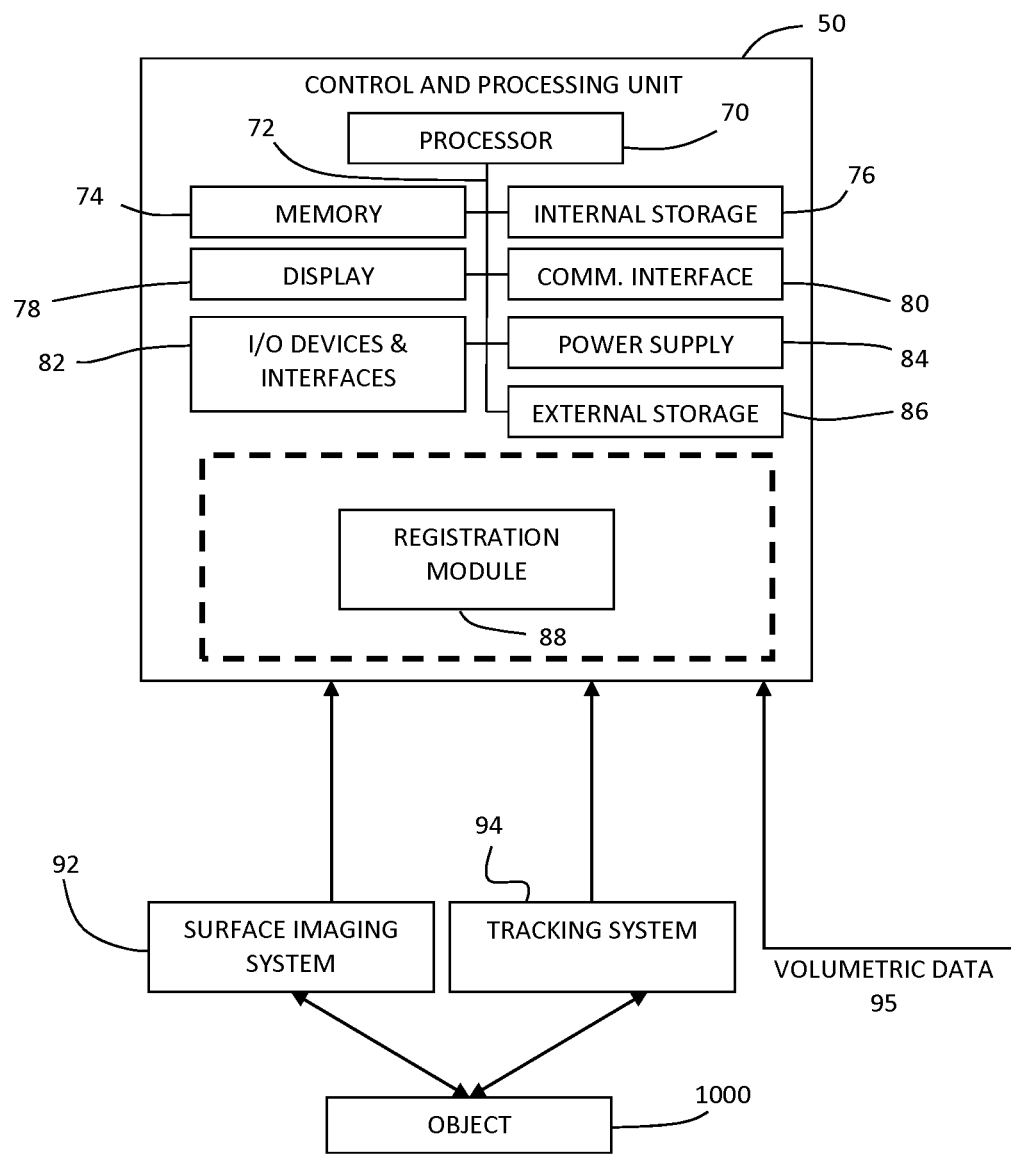
FIG. 1B is a block diagram illustrating an example system configuration, including various example components of a control and processing unit.

FIG. 1B provides a block diagram illustrating an example implementation of a system for surface imaging. Volumetric data 95 is provided to control and processing unit 50 for registration to intraoperatively acquired surface data. Surface imaging system 92 scans object 1000, and surface topology data is provided to control and processing unit 50, which is registered with volumetric image data 95. Tracking system 94 is employed to track the positions and orientations of surgical instruments, and of a tracking marker support structure, as described below. A calibration transformation is determined between the reference frames of the surface imaging system 92 and the tracking system 94.

Surface imaging system 92 may be any suitable system for detecting, measuring, imaging, or otherwise determining the surface topology of one or more objects using optical radiation or sound waves (e.g. ultrasound). Non-limiting examples of suitable optical devices include laser range finders, photogrammetry systems, and structured light imaging systems, which project surface topology detection light onto a region of interest, and detect surface topology light that is scattered or reflected from the region of interest. The detected optical signals can be used to generate surface topology datasets consisting of point clouds or meshes. Other examples using sound waves for determining surface topology can include ultrasonography.

FIG. 1B also provides an example implementation of control and processing unit 50, which includes one or more processors 70 (for example, a CPU/microprocessor or a graphical processing unit, or a combination of a central processing unit or graphical processing unit), bus 72, memory 74, which may include random access memory (RAM) and/or read only memory (ROM), one or more internal storage devices 76 (e.g. a hard disk drive, compact disk drive or internal flash memory), a power supply 84, one more communications interfaces 80, external storage 86, a display 78 and various input/output devices and/or interfaces 82 (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a position tracked probe, a foot switch, and/or a microphone for capturing speech commands).

Control and processing unit 50 may be programmed with programs, subroutines, applications or modules, which include executable instructions, which when executed by the processor, causes the system to perform one or more methods described in the disclosure. Such instructions may be stored, for example, in memory 74 and/or internal storage 76. In particular, in the example embodiment shown, registration module 88 includes executable instructions for generating performing image registration. For example, registration module 88 may include executable instructions for performing the methods disclosed herein, such as the methods illustrated in FIGS. 11A, 11B, 13A, 20 and 21.

Although only one of each component is illustrated in FIG. 1B, any number of each component can be included in the control and processing unit 50. For example, a computer typically contains a number of different data storage media. Furthermore, although bus 72 is depicted as a single connection between all of the components, it will be appreciated that the bus 72 may represent one or more circuits, devices or communication channels which link two or more of the components. For example, in personal computers, bus 72 often includes or is a motherboard. Control and processing unit 50 may include many more or less components than those shown.

In one embodiment, control and processing unit 50 may be, or include, a general purpose computer or any other hardware equivalents. Control and processing unit 50 may also be implemented as one or more physical devices that are coupled to processor 70 through one of more communications channels or interfaces. For example, control and processing unit 50 can be implemented using application specific integrated circuits (ASICs). Alternatively, control and processing unit 50 can be implemented as a combination of hardware and software, where the software is loaded into the processor from the memory or over a network connection. For example, connections between various components and/or modules in FIG. 1A, which enable communications of signals or data between various systems, may be a direct connection such as a bus or physical cable (e.g. for delivering an electrical or optical signal), such a LAN or WAN connections, or may be a wireless connection, for example, as an optical transmission modality, or wireless transmission modality such as Wifi, NFC or Zigbee®.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refers to all computer-readable media, except for a transitory propagating signal per se.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

In order to combine the tracking data with the surface data for surgical navigation, a calibration procedure is required, which relates the coordinate system of the tracking system to that of the surface imaging system. If the relative position of the tracking system and the surface imaging system is fixed, this calibration may be performed by obtaining the position of at-least 3 points from a calibration object from both systems, and aligning these points to obtain the calibration transformation, as described in International Patent Application No. PCT/CA2011/050257.

In an alternative embodiment, as disclosed in International Patent Application No. PCT/CA2011/050257, the surface imaging device may have fiducial markers attached to it, which may be tracked by the tracking system. In this configuration, a calibration procedure can be used to obtain the calibration transformation from the coordinate system of the surface system to the attached fiducial markers. The calibration transformation between the coordinate system of the tracking system and the surface imaging system is then continuously updated as the position of surface imaging device is changed.

After calibration, the calibration transformation between the coordinate system of the tracking system and the surface imaging system is known. Registering the surface datasets and volumetric image data is therefore equivalent to identifying the position of the volumetric image data in the coordinate system of the tracking system. As a result, any medical instrument 40, which is afterwards tracked with the tracking subsystem, can be presented to the surgeon as an overlay 55 of the surgical instrument 40 on the registered 3D image data on a display 60 or other visualization devices.

A number of factors can affect the ongoing validity of the calibration transformation. For example, if the system were to undergo a significant mechanical impact, the relative positioning of the surface imaging system and the tracking system may shift slightly. In another example, the transformation may be dependent on the ambient temperature in which it is operating and thus only valid within a specified range of ambient temperatures. In both of these examples it would be advantageous to validate the accuracy of the calibration transformation and/or generate a new calibration transformation at the time of use without impacting the surgical workflow.

While much of the discussion which follows assumes the use of a system having two subsystems (tracking and surface imaging), it is noted that alternative system configurations may be employed to perform simultaneous tool tracking and acquisition of anatomical surfaces using an integrated system, for example by identification of surface topology on tools, as described in International Patent Application No. PCT/CA2011/050257. In another example system configuration, a system can utilize a common pair of cameras for tool tracking (e.g. via glyphs or reflective spheres) and surface imaging (e.g. in either the visible or IR). Using the same camera systems for both tool tracking and surface imaging eliminates the need for the calibration between the two systems described above.

To compensate for patient or system motion, it is also advantageous to use a tracked device attached to the patient's anatomy (e.g. to a skeletal feature of the patient's anatomy). Accordingly, as shown in FIG. 1, the position of a tracking marker support structure 45 is recorded by the tracking system at the same time (i.e. within a time duration that is sufficiently small to preclude errors associated with patient motion) as when the surface dataset is acquired. The surface dataset is transformed to the coordinate system of tracking system (using the previously acquired calibration transformation), and then registered to the volumetric image data. Subsequent tracking of surgical instruments relative to the volumetric image data can be performed relative to the tracked tracking marker support structure, with compensation for patient or system motion, without the need for continuous acquisition of surface data.

During a surgical procedure, it is generally preferred that tracking marker support structure 45 should not block the line-of-sight on the surgical target for the surgeon. The risk of possible obstructions of the surgeon's movement should be minimized especially when other tracked medical instruments are in the surgical field, where the tracking attachments could shadow each other. It would also be beneficial for the surgeon to be able to securely attach and to remove the tracking marker support structure with relative ease. This is particularly important for spine surgery, where normally more than one vertebra are instrumented and the risk of misplacing by accidentally touching the tracking marker support structure by the surgeon is high. Furthermore, in order to minimize costs, a re-useable and sterilizable tracking marker support structure 45 is preferred. This can be achieved by use of appropriate materials like for example stainless steel, tungsten carbide or titanium.

For surgical guidance using a combination of a tracking system and a surface imaging system (as illustrated in the example system shown in FIG. 1), it will be understood that in order to acquire surface image data, tracking marker support structure 45 should not block the line-of-sight on the surgical target for the structured light system. To achieve registration with the volumetric image data, the surface imaging system should cover the anatomical site of interest in a way that the characteristic anatomy is represented in the acquired surface data. For example in a navigated spine procedure, it will aid registration if the acquired surface captures the surfaces of the lamina and the spinous process in order to optimize the registration for a particular level of the spine (vertebrae). However, a tracking marker support structure can obstruct the visibility of the boney surfaces to the surface imaging system.

Attaching the tracking marker support structure to an adjacent vertebral level can avoid obstruction of the line-of-sight, but this can reduce the accuracy of the navigation, since the spine is flexible and the relative positions of the vertebras can change between the acquisition of the preoperative images and when the patient is on the operating table. Therefore, it is beneficial to have a tracking marker support structure that can be securely attached to the vertebrae that is being operated on, while minimally obstructing the line-of-sight of the surface imaging system to the relevant structures of that vertebrae.

Figure 2:
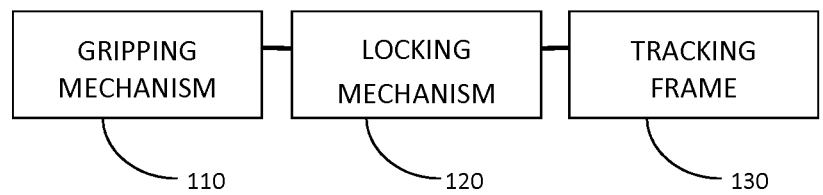
FIG. 2 shows an example block diagram showing the components of a tracking marker support structure.

FIG. 2 schematically illustrates an example tracking marker support structure 45 used for surgical guidance combing a tracking system and a surface imaging system for performing navigated spinal surgery. Example tracking marker support structure 45 is shown including removably attachable gripping mechanism 110, which firmly and removably attaches to the vertebrae of interest and avoids or reduces the obscuring of the relevant surfaces—the top of the spinous process and the laminas—from the line-of-sight of the surface system and the surgeon. Tracking marker support structure 45 is also shown including locking mechanism 120, which ensures that the tracking marker support structure 45 remains securely attached to the vertebrae and can be readily attached and removed. Tracking marker support structure 45 is also shown having tracking frame 130 that includes fiducial/tracking markers, which are tracked by tracking system 94. As noted above, tracking frame 130 should not interfere with the surgeon's use of tools in the vicinity of the vertebrae to which tracking marker support structure 45 is attached.

Figure 3A:
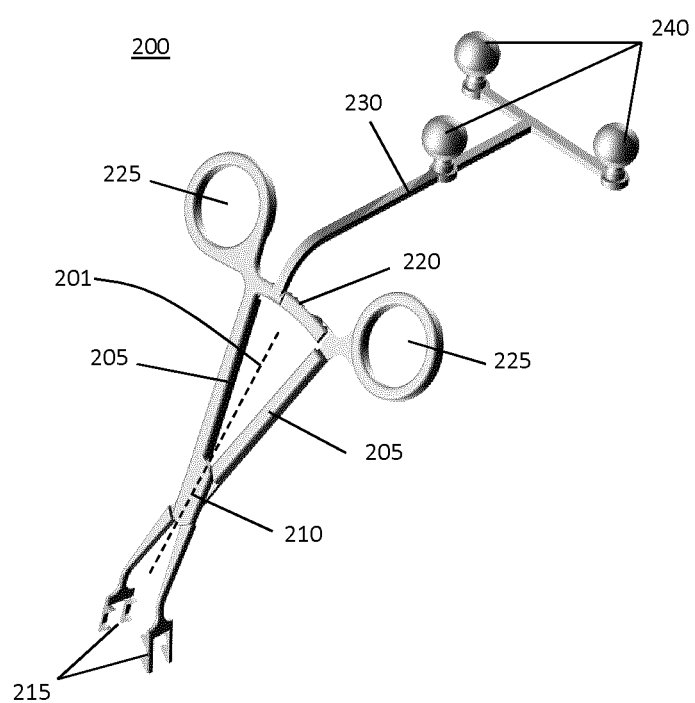
FIGS. 3A and 3B provide an (A) isometric and (B) top view of an example embodiment of a tracking marker support structure.

FIG. 3A shows an example implementation of a tracking marker support structure 200 which meets the above criteria for a combination of tracking and surface imaging. This tracking marker support structure 200 is based on a bone clamp design. It employs forceps (which may be referred to as a pair of forceps) comprising two members 205 that define longitudinal axis 201 and pivot around a pin 210, such that jaws 215 with spikes are rotated to grip the spinous process.

Figure 3B:
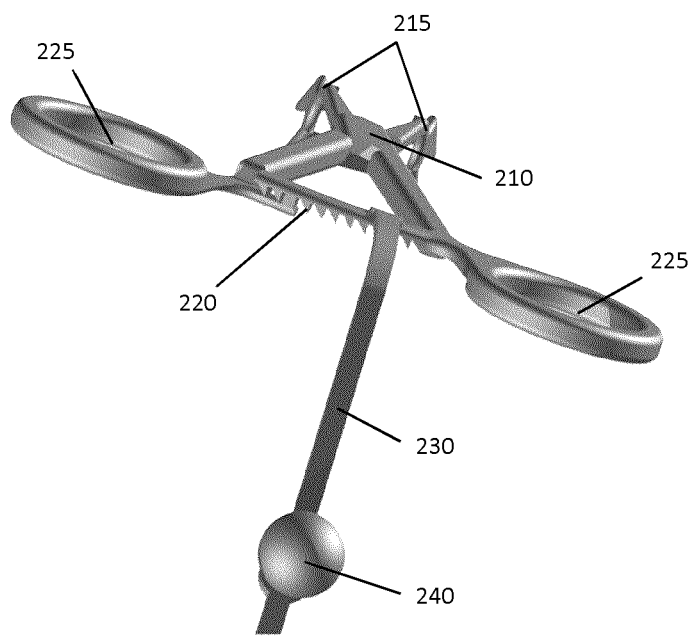

As shown in FIG. 3B, a locking mechanism is operably connected to the forceps. In the present example implementation, the locking mechanism includes a series of interlocking teeth 220 cooperates with two handles 225 on the other end of the members 205 to allow the surgeon to tighten and to lock tracking marker support structure 200 in place.

As shown in FIG. 3A, marker attachment 230 is provided that includes tracking (fiducial) markers near a distal region thereof, where a proximal end of marker attachment 230 is mechanically coupled (e.g. attached, connected, or integrally formed) the forceps at a location that is remote from the location of clamping jaws 215, in order to allow the tracking system to track the position of the tracking marker support structure. In the present example implementation, the tracking frame is mechanically coupled to one of the interlocking teeth 220, but it will be understood that marker attachment 230 may be mechanically coupled to other portions of the forceps, such as to one of the handles, or to one of longitudinal members 205. In this example embodiment, three passive reflective spheres are used as markers 240 for tracking the position of the tracking marker support structure. However, as noted above, it will be understood that other configurations and types of fiducial markers may be employed.

Figure 4:
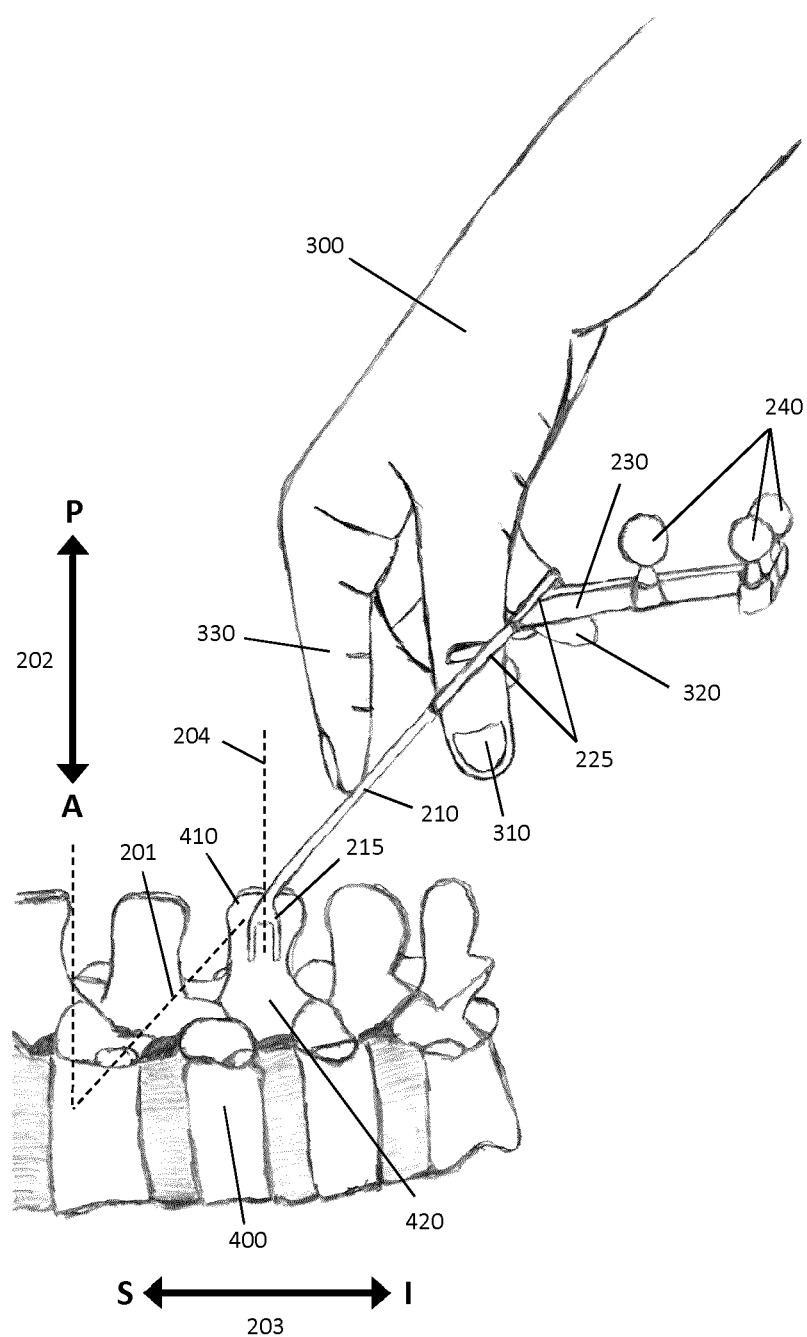
FIGS. 4 and 5 provide side and top views, respectively, of the use of an example tracking marker support structure for clamping the tracking marker support structure in a pre-configured orientation.

For clamping, the surgeon holds the tracking marker support structure 200 with one hand 300 as indicated in FIG. 4. For example, the surgeon may place the thumb 310 and the middle finger 320 through the two handles 225. The index finger 330 may be employed to push against pivot pin 210, which helps to further stabilize the clamp 200 inside the surgeon's hand 300.

As can be clearly seen in FIG. 3A and in FIG. 4, marker attachment 230 is angled, relative to longitudinal axis 201, in a direction toward the patient anatomy, thereby ensuring that the surgeon's hand 300 will not contact marker attachment 230 or the markers 240 during clamping. This is a useful feature of the tracking marker support structure 200 because the surgeon's hand 300 might be covered by blood or other liquids, which could block the markers 240 and cause interference with the tracking system.

To attach or detach the tracking marker support structure 200 to the spinous process, the surgeon will adjust the clamping force of the interlocking teeth 220 using the handles 225 and therefore the grip of the jaws 215 onto the interlocked bone. This locking mechanism can allow the surgeon to change the position of the tracking marker support structure 200 between two spinous processes in a short duration, for example, less than 10 seconds.

Figure 5:
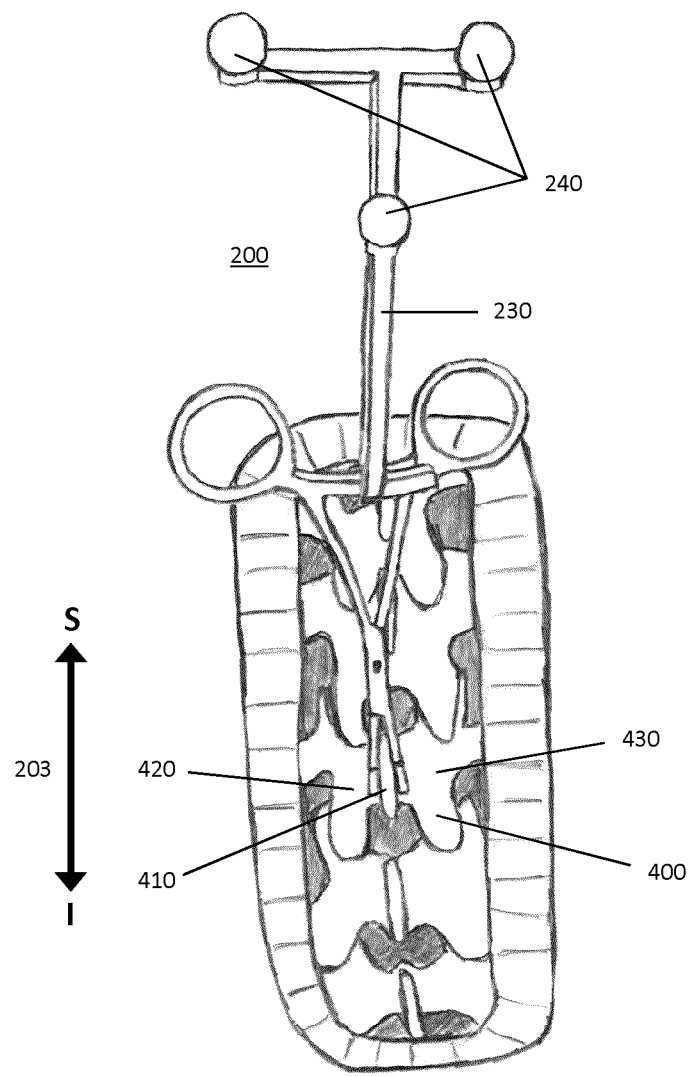

As shown in FIGS. 4 and 5, the members 205 of the forceps extend from the clamping jaws 215 such that when the clamping jaws are clamped to the spinous process 410 of the vertebra of interest 440, the longitudinal axis 201 associated with the forceps is angled relative to the Anterior-Posterior (AP) direction 202 that is associated with the subject, wherein the normal direction lies in the sagittal plane and is perpendicular to the Superior-Inferior (SI) 203 direction of the spine, such that a skeletal region 420 or 430 adjacent to the skeletal feature is unobstructed by the forceps, thereby permitting overhead surface data acquisition of the skeletal region.

In the example embodiment shown in FIGS. 3A and 4, clamping jaws 215 are characterized by a normal axis 204 that is configured to be perpendicular to the SI direction 203 of the spine when the clamping jaws 215 are clamped to the spinous process 410. The jaws 215 are therefore configured to uniquely clamp to the spinous process 410 in a preselected orientation, such that the normal axis 204 of the clamping jaws 215 coincides with the AP direction 202. Accordingly, the attachment of tracking marker support structure 200 to the patient establishes a reference direction that is associated with the intraoperative orientation of the patient. As described below, this reference direction can be employed to guide the initial registration process between a surface that is intraoperatively acquired by a surface imaging system and volumetric imaging data.

FIG. 5 shows the example tracking marker support structure 200 securely attached to the spinous process 410 of a vertebrae 400. In this configuration, tracking marker support structure 200 is not blocking the view of the surgeon onto the spinous process 410 and the left or the right lamina 420 and 430 respectively, and maintains a clear imaging field for the surface imaging system. In addition, the marker attachment 230 with the markers 240 is clearly visible to the tracking component of the combined navigation system.

Figure 6A:
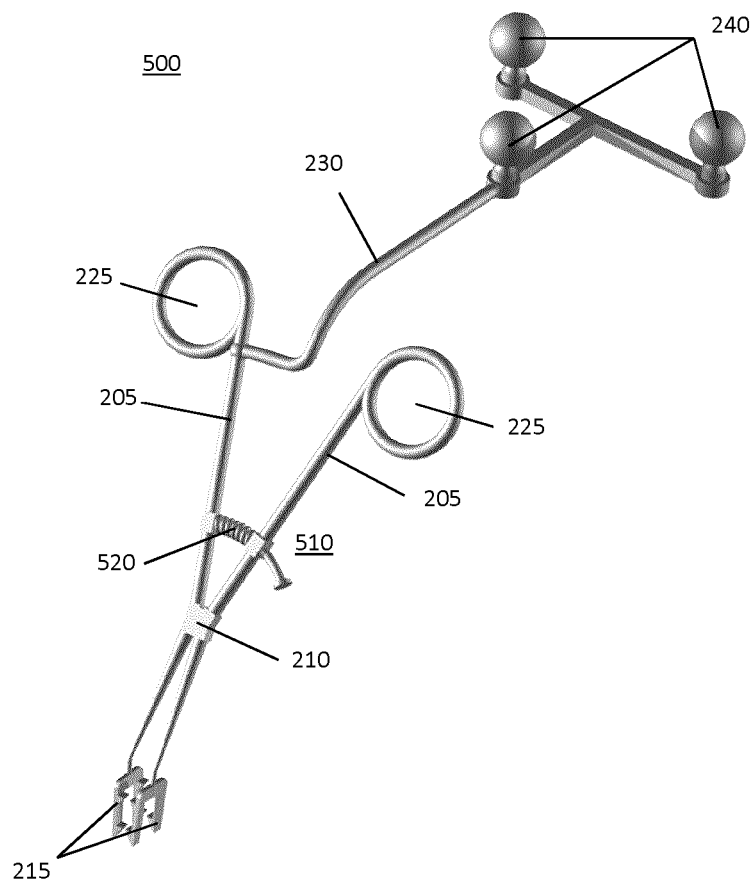
FIGS. 6A and 6B illustrate an example embodiment of a tracking marker support structure that employs a spring locking mechanism, where FIG. 6B provides a detailed view of the spring locking mechanism.
Figure 6B:
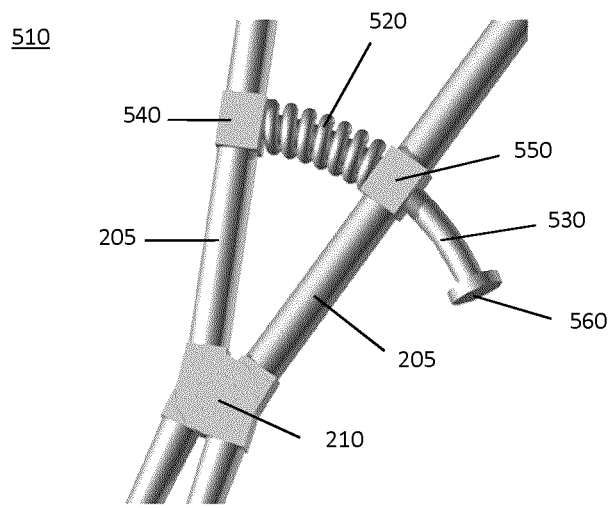

It will be understood that the locking mechanism shown in FIG. 2 is but one example of a suitable locking mechanism, and that a wide variety of alternative locking mechanisms may be employed. For example, FIG. 6A, illustrates an example embodiment of a tracking marker support structure 500 that employs a spring locking mechanism 510. An extension spring 520 pushes the two members 205 together, which tightens the jaws 215 on the opposite side of the pivot pin 210. The marker attachment 230 with the markers 240 is connected to one of the members 205. As shown in a more detailed view in FIG. 6B, extension spring 520 has a guidance wire or pin 530 that is received within extension spring 520. Guidance wire 530 is connected to one spring stopper 540 on one of the members 205 and passes through a hole or aperture in second spring stopper 550 on the other member 205. Another stopper 560 on the guidance wire 530 restricts the range possible movement of members 205. In order to attach the tracking marker support structure 500 to a spinous process, the surgeon opens the clamp by pushing apart the handles 225 and holds the reference close to the desired position on the spinous process. When the handles 225 are released, the extension spring 520 is automatically clamping the tracking marker support structure 500 onto the spinous process.

Figure 7A:
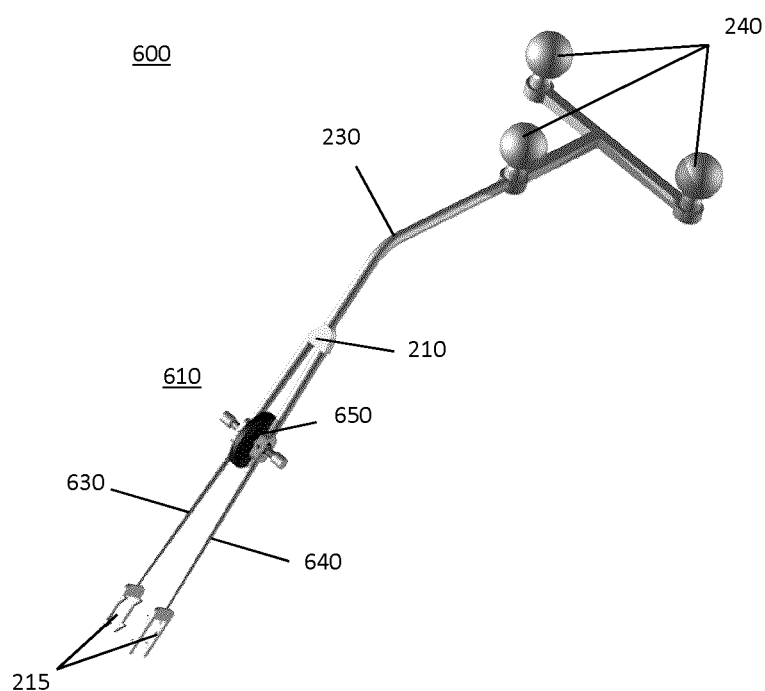
FIGS. 7A and 7B illustrate an example embodiment of a tracking marker support structure that employs a thumb-screw mechanism, where FIG. 7B provides a detailed view of the thumb-screw mechanism.
Figure 7B:
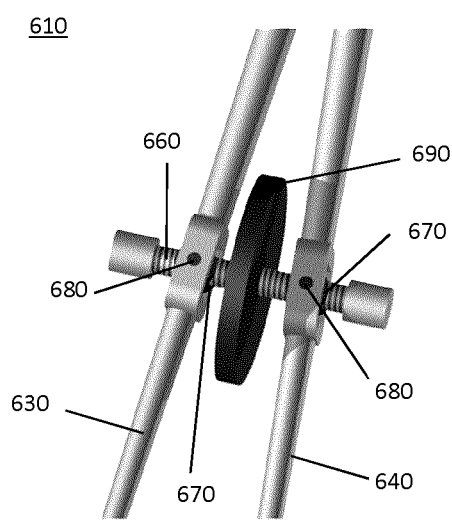

FIG. 7A shows another example implementation of a tracking marker support structure 600, which may be used for combined tracking and structured light imaging. Again, two longitudinal members, 630 and 640 respectively, with jaws 215 for clamping onto the bone are connected via a pivot pin 210. In the present example embodiment, the marker attachment 230 with the markers 240 is a rigid extension of one of the members 630 beyond the pivot pin 210. A thumb-screw mechanism 610 is used to tighten or loosen the grip of the clamp onto the bone and to lock jaws 215 in place. The mechanism is shown in more detail in FIG. 7B. A threaded spindle 660 is positioned between two cylinder holders 670, which are connected to the two members 630 and 640 of the clamp by a rotational axis 680. The surgeon can attach or detach the tracking marker support structure 600 using the rotation wheel 690 on the spindle 660. The thread on the spindle 660 is self-locking so that the attachment of the tracking marker support structure 600 is secure when the rotation wheel 690 is not used.

Figure 8A:
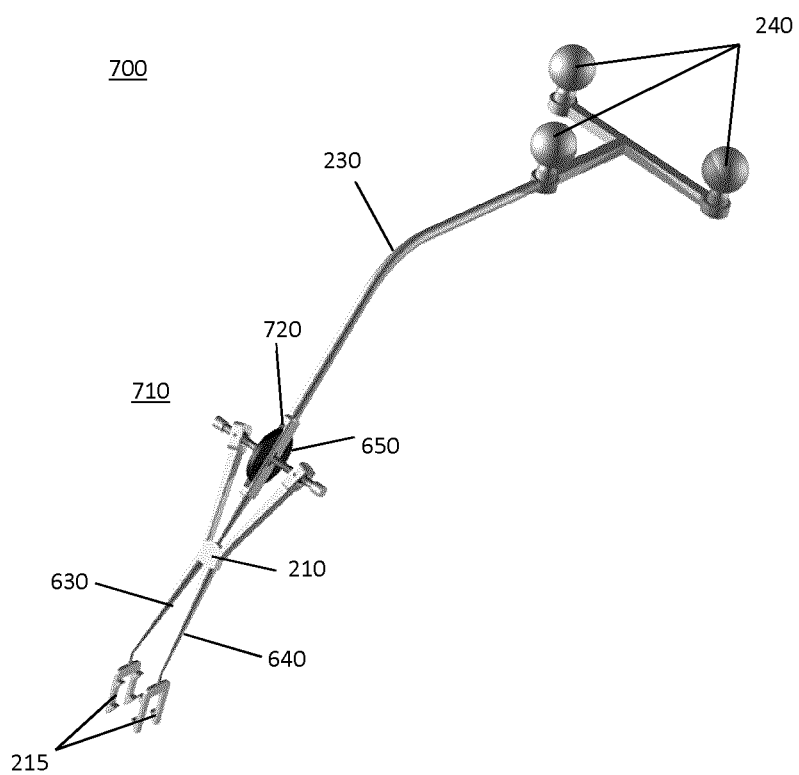
FIGS. 8A and 8B illustrate an alternative example embodiment of a tracking marker support structure that employs a thumb-screw mechanism, where FIG. 8B provides a detailed view of the thumb-screw mechanism.
Figure 8B:
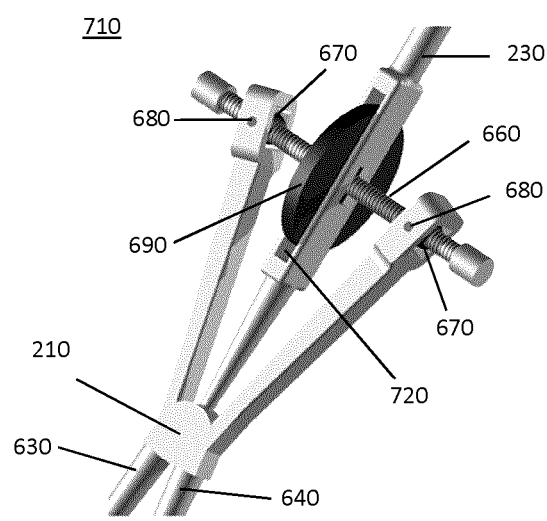

In an alternative example implementation, instead of positioning the thumb-screw mechanism 610 and the clamping jaws 215 on the same side of the pivot pin 210, they can be on opposite sides. For example, in the embodiment shown in FIG. 8A, the marker attachment 230 with the markers 240 of tracking marker support structure 700 is connected directly to the pivot pin 210 and integrates the rotation wheel 650 of the thumb-screw mechanism 710 using a slit 720 (for detailed view see FIG. 8B).

The three example locking mechanisms described above (interlocking teeth, extension spring and thumb-screw) allow an easy, fast and secure attachment of the tracking marker support structure to the spinous process. However, as noted above, persons skilled in the art will understand that similar locking mechanisms may be employed.

FIGS. 9A-I show different jaw 215 designs for the gripping mechanism 110 (see FIG. 2), which could be used, for example, to attach the tracking marker support structure to a spinous process. FIG. 9A and show a rectangular plate configuration for gripping flat surfaces such as those found in the lumbar and lower thoracic region of the spine. The surface is carrying a number of coned spikes, which increase the grip when the jaw is pressed onto the bone. The number and position of spikes may vary for the specific design. The connection to the member 205 is on the short side of the rectangular plate. However, it will be understood that this connection could be also be made on the long side of the rectangular plate, for example, as shown in FIGS. 9C and D, if the tracking marker support structure should be employed for shorter spinous processes.

In other embodiments, the jaws may be configured to include two or more fingers. For example, FIGS. 9E and F show an example two finger configuration which is more suitable for rough bone surfaces. FIGS. 9G to I show an alternative example two finger configuration with four sloped spikes.

Figure 10A:
FIGS. 10A-H shows additional example implementations of clamping jaws based on curved plates.

FIGS. 10A-H shows additional example jaw 215 designs based on curved plates. An example angled bracket gripping plate, as shown in FIGS. 10A and B are more suitable for gripping the rounded spinous processes located in the upper thoracic and cervical regions of the spine.

Figure 10C:

FIGS. 10C and D show a curved bracket also useful for the upper thoracic and cervical regions of the spine.

Figure 10E:
Figure 10G:
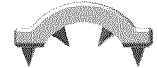
Figure 10B:
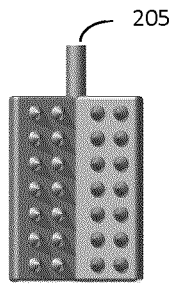
Figure 10D:
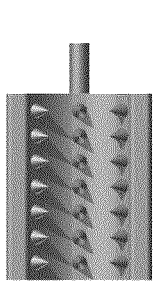
Figure 10F:
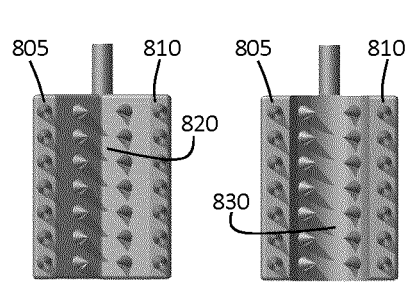
Figure 10H:
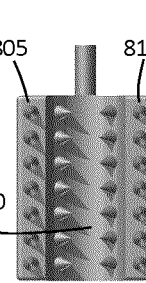

FIGS. 10E to H show a number of gripping plate configurations which are capable of achieving good grip in any region of the spine due to the combination of a flat plate region and curved or angled structures. More specifically, the example gripping plate (jaw) configurations shown in FIG. 10F and FIG. 10H each include co-planar flat surfaces 805 and 810, and also include an inwardly directed surface connecting the two outer flat surfaces 805 and 810, such that the clamping jaws are configured for clamping to a wide range of spinous process geometries. In FIG. 10E, the inwardly directed surface 820 is formed from two planar surface segments. FIG. 10H illustrates an alternative implementation in which the inwardly directed surface 830 is a curved surface. The outer flat surfaces 805 and 810 and the inwardly directed surfaces 815 and 820 each comprise spikes.

It will be understood that the clamping jaw configurations shown in FIGS. 9A-I and FIGS. 10A-H may be provided with any type of surgical clamping device, irrespective of whether or not the clamping device includes a tracking frame. Furthermore, those skilled in the art will understand that a wide variety of alternative jaw (gripping plate) geometries and configurations may be employed in addition to the example implementations shown in FIGS. 9A-I and FIGS. 10A-H.

In the example embodiments provided below, examples of the use of a tracking marker support structure during surgical guidance are described. It will be understood, however, that the use of the tracking marker support structure, and the methods below, while being explained within the example context of spinal surgical procedures, may be adapted to, and employed in, a wide range of other surgical procedures. Examples of additional surgical procedures that may benefit from the use of the present devices and methods disclosed herein are provided below.

In the present non-limiting example, at the beginning of a navigated posterior approach spine surgery, the patient is placed in a prone (face-down) configuration on the operating table (see FIG. 1) and anesthesia is administered. The surgeon approaches the spine of the patient from the back and exposes the boney surface of the vertebrae of interest by retracting soft tissue components.

Figure 11A:
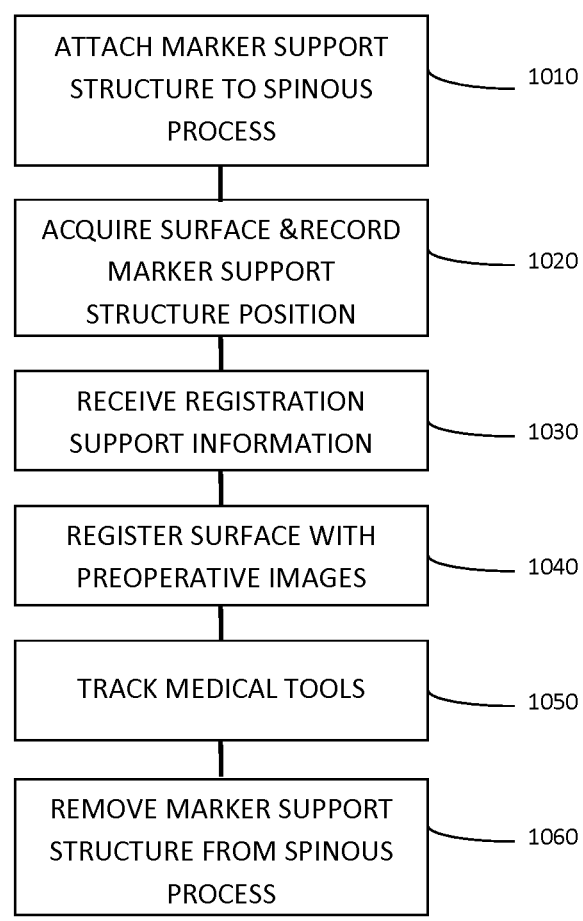
FIG. 11A is a flow chart illustrating an example method of employing a tracking marker support structure to support the registration of intraoperatively acquired surface data to volumetric (e.g. pre-operatively acquired) image data.

Preparing the patient, the navigated portion of the surgery begins, which is illustrated in the example flow chart shown in FIG. 11A. In step 1010, the tracking marker support structure 45 is securely attached to the spinous process of the vertebrae to be navigated. In step 1020, the surface imaging system (such as a structured light system) acquires a surface scan of the vertebrae, and the tracking system is employed to record the position of the tracking marker support structure 45 using triangulation of the markers (e.g. passive optical fiducial markers 240 shown in FIG. 3A).

In step 1030, surgical guidance system may be provided with registration support information that may be to facilitate and/or improve the efficiency or accuracy of the registration of the acquired surface to the volumetric (e.g. pre-operatively acquired) image data (as described in further detail below). In step 1040, the registration process utilizes the acquired surfaces of the visible lamina and/or spinous process regions and the registration support information to register the volumetric image data (e.g. from a CT scan).

Once the registration is complete, the system can present an overlaid image, as shown in step 1050, of any tracked tool relative to the registered volumetric image data for navigation of the surgical procedure on the vertebrae (e.g. insertion of pedicle screws). The tracking marker support structure allows the surgical guidance system to detect, and compensate for, any movement (due to respiration, patient movement, or system movement) of the vertebrae during the navigation, without requiring acquisition and registration of additional surface data to the volumetric image data. In step 1060, the surgeon removes the tracking marker support structure from the vertebrae and optionally restarts the process on the next vertebra if desired. This process may thus be repeated one or more times to address one or more vertebral levels.

Figure 11B:
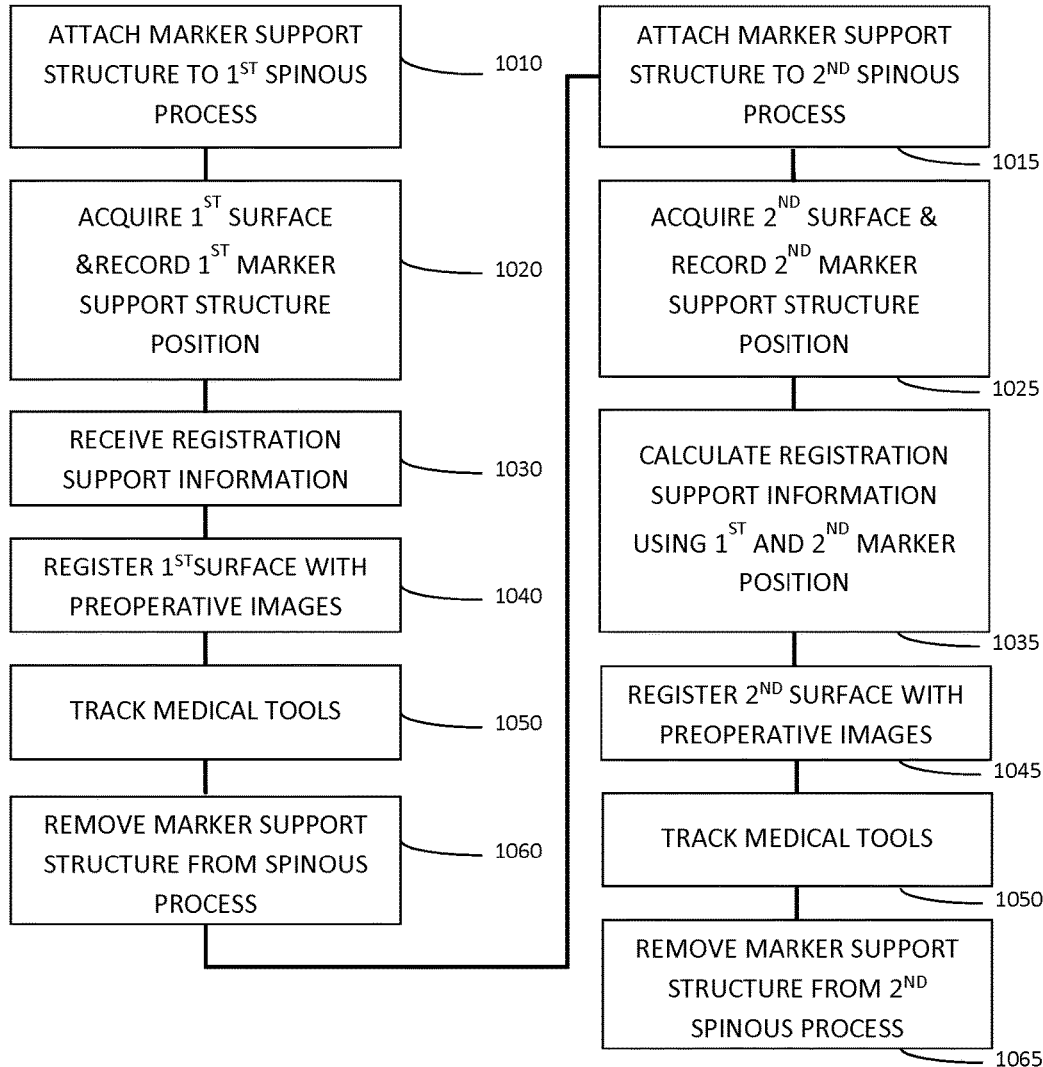
FIG. 11B is a flow chart illustrating an example method of employing a tracking marker support structure to support the registration of intraoperatively acquired surface data to volumetric image data for multiple vertebral levels.

FIG. 11B illustrates an example method for performing registration when the aforementioned process is repeated for an additional vertebral level. In this example method, the method of clamping and registering to a $1^{st}$ spinous process shown in FIG. 10A is repeated. However, after removal of tracking marker support structure 1060, the tracking marker support is re-clamped to a $2^{nd}$ spinous process 1015. In step 1025 a second surface scan and position is recorded by the surface imaging system and tracking system respectively. Position data from the tracking system acquired in step 1020 from the $1^{st}$ vertebral body is combined with position data acquired in step 1025 from the $2^{nd}$ vertebral body to calculate additional registration support data 1035. Examples of such data include estimates of axial direction of the spine (can be used as an initial condition for the registration 1040) and the approximate spacing between vertebral bodies (which can be used to specify cropping region for the registration procedure 1040). It is noted that even if the tracking marker support is not moved to an adjacent level, it is still possible to estimate the mean distance between vertebral bodies since standard practice ensures the surgeon always specifies (through a user interface element) the level on which they have placed the clamp.

In one example implementation of the process illustrated in FIGS. 11A and 11B, the surgeon or system operator may be queried to provide the registration support information. For example, in step 1030, the surgeon or system operator may be requested to indicate a set of matched point pairs on the pre-operative scan and the patient's body as initial information to guide the registration process (for example, three point pairs may be requested and provided). The points can be selected, for example, on the patient's body using a tracked tool touching the patient's anatomy, or virtually on the acquired surface (touch-less registration). Typical point selection for spine surgery may include 1 point on each of the left and right lamina and top of the spinous process (or the ligament which runs over it).

In another embodiment, a set of different registration support information could be provided and employed in step 1030. For example, one piece of registration support information could be information specifying a particular anatomical direction in the acquired surface, for example the head-foot (superior-inferior) direction.

Figure 12A:
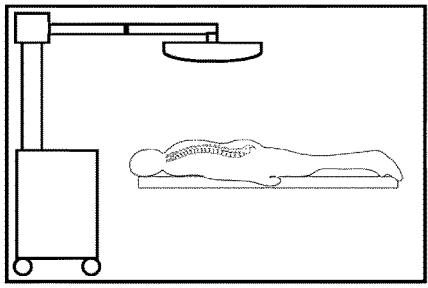
FIG. 12A illustrates an example screenshot that can be employed for obtaining information regarding the intraoperative position of a patient.

This information can be obtained by querying the surgeon or operator, or for example, by inferring this direction through the positioning of the system relative to the patient. For example, if the system is positioned near the head of the operating table then the head-foot direction can be estimated with sufficient accuracy for registration. FIG. 12A shows an example of graphical user interface, where the surgeon or system operator can specify the orientation of the system at the start of the surgery. This information can be used together with the known patient positioning during the pre-operative imaging (which is normally stored inside the data header) as registration support information (i.e. a priori information) to support the registration process.

In addition or alternatively, the surgeon or system operator can be queried to enter the procedure specific information (e.g. surgery type, patient positioning, surgical approach or incision orientation) at the start of the surgery using a graphical user interface similar to the one shown in FIG. 12A. For example, a patient undergoing a posterior approach spine surgery will be in a prone (face down) position on the operating table, which allows to infer the anterior-posterior direction in the acquired surface (since the system is always located above the patient). This information could alternatively be obtained based on a pre-determined surgical plan.

Another form of registration support information could be one matched point pair selected on the pre-operative scan and the patient's body or acquired surface. A convenient point for a matched point pair could be the top of the spinous process of the vertebrae of interest. Instead of asking the surgeon or system operator to select the point on the spinous process, the known attachment point of the tracking marker support structure can be used. Assuming that the attachment point of the clamp is always to the spinous process, the location of the spinous process on the patient can be approximated using the tracked tracking marker support structure position from the tracking system.

In several of the embodiments described herein, the tracking marker support structure is configured to be attached a given skeletal feature in a known relative orientation. The skeletal feature may be a skeletal projection, such as a spinous process. Such a skeletal feature has, associated therewith, a known anatomical direction in the sagittal plane. For example, in the example application of spinal surgical procedures, the tracking marker support structures described herein are configured to clamp to the spinous process such that the tracking marker support structure is attached to the patient anatomy in a fixed position and orientation relative to the point of attachment. For example, the tracking marker support structure shown in FIG. 5 is configured to clamp onto the spinous process in a pre-selected orientation that automatically determines the inferior-superior direction of the spine.

This known orientation of the tracking marker support structure, relative to the patient anatomy, allows for the determination of an intraoperative reference direction associated with the intraoperative position and orientation of the patient. This intraoperative reference direction may then be used, optionally with additional registration support information (such as one or more matched point pairs), as an input to the registration process, in order to improve the efficiency and/or accuracy of the registration process. As noted above, as the volumetric image data typically has orientation information in a header file, and therefore, determining an intraoperative reference direction associated with the intraoperative patient orientation, and thus the intraoperative orientation of the acquired surface, can be beneficial in increasing the efficiency and/or accuracy of the registration process.

For example, the intraoperative position and orientation of the patient (or at least of the local anatomical region of interest) can be determined based on the measured position of the tracking marker support structure, due to the known orientation of the tracking marker support structure relative to the skeletal feature, and the calibration transformation between the reference frame of the surface imaging device and the reference frame of the tracking system.

A full set of registration support information that is sufficient for the registration process may require a combination of the above mentioned types of registration support information. As noted above, in some embodiments, the registration support information may include information associated with the position and/or orientation of the tracking marker support structure, such as the position of attachment (that is associated with a known anatomical feature), and/or the orientation of the tracking marker support structure relative to the orientation of the known anatomical feature.

The surface imaging system has generally a field of view that is much larger than the exposed vertebrae of interest in order to enable the surgeon to operate on multiple vertebrae levels without having to reposition the system each time. The additional surface regions outside the immediate vicinity of the vertebrae of interest generally do not help with the registration. Indeed, these additional surface regions can be detrimental, potentially causing an incorrect registration, if the spine in the operating room is not in the same position as during the pre-operative imaging or if soft tissue surfaces at the surgical incision borders are scanned.

In one example embodiment, the tracking marker support structure 45 is used to provide a spatial reference to determine where to segment the acquired surface, so that only the immediate surroundings of the vertebrae of interest is kept for registration.

Before this segmentation is performed, the spatial position of the tracking marker support structure 45 from the tracking system is first transformed into the coordinate system of the surface imaging system using the known calibration transformation between the two systems. The segmentation is then performed by cropping the surface data using a suitable mask within spatial region or within a prescribed distance associated with the position of attachment of the tracking marker support structure. For example, a spherical mask surrounding the point of attachment may be employed to determine the spatial region over where the acquired surface is to be cropped as per the segmentation process.

This segmentation creates a partial surface covering mainly the vertebrae of interest for the registration. Other masking geometries can be used for the cropping of the surface data. Examples are rectangular boxes, cylindrical discs or other types of prisms with the main axis aligned to the spine, where the alignment can be determined from the position of the clamping axis of the tracking marker support structure, which is aligned with the spinous process.

Examples of such cropping structures are shown in FIGS. 12B-12G and include spherical, cigar shaped and patient specific cropping masks. In these examples it is useful to define the marker support structure tracking point 206 at the intersection of jaws 215 and members 210 on the member connecting rigidly to marker attachment 230.

Figures 12B, 12C:
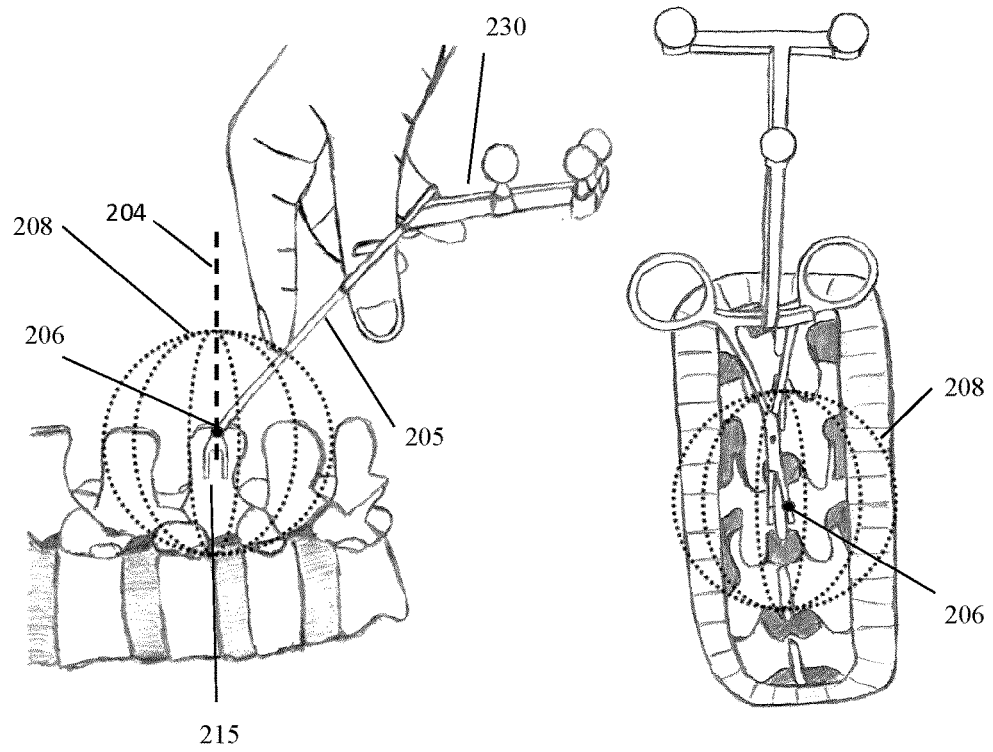
FIG. 12B-I illustrate the use of different cropping masks which may be employed for the segmentation of a surface within a spatial region or within a prescribed distance associated with the position of attachment of the tracking marker support structure.
Figures 12D, 12E:
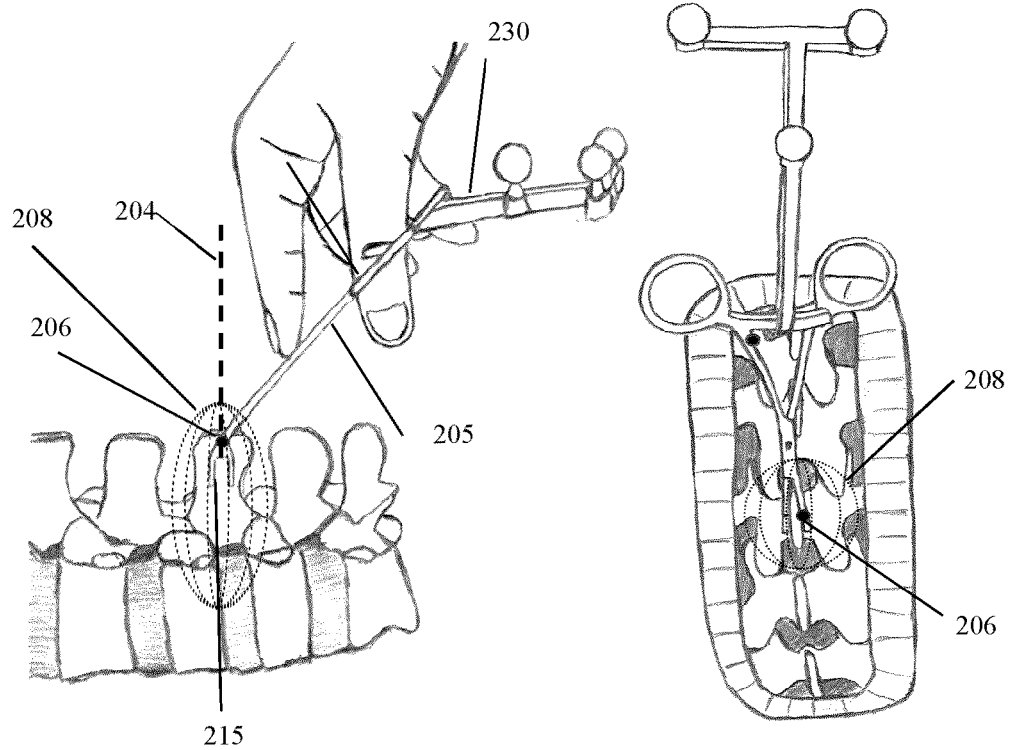
Figures 12F, 12G:
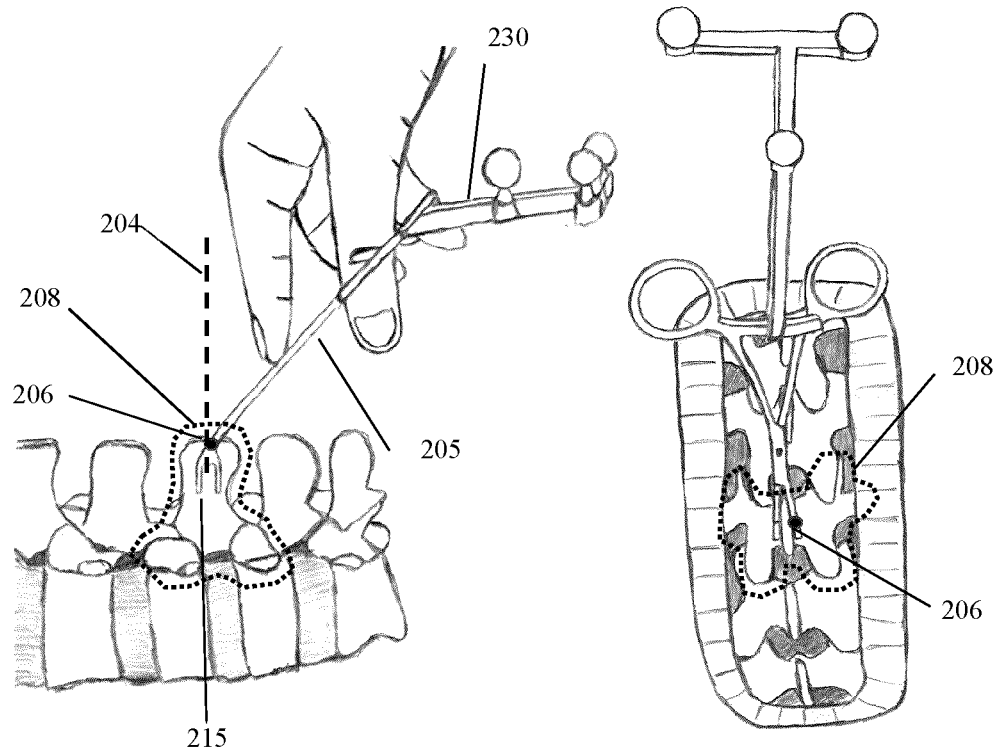
Figures 12H, 12I:
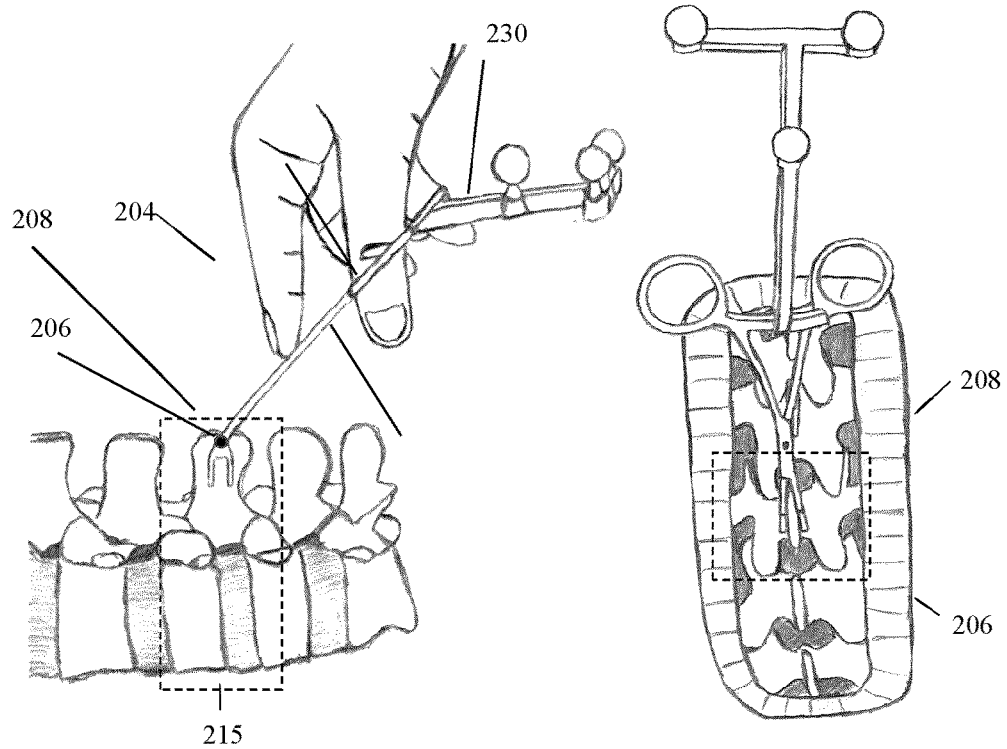

In FIGS. 12B and 12C, a spherical cropping region 208 is shown centered on marker support structure tracking point 206. In FIGS. 12D and 12E, a cigar shaped cropping mask 208 not centered on maker support structure tracking point 206 is shown. In FIGS. 12F and 12G, a patient specific cropping mask generated from CT scan data is shown. Lastly, in FIGS. 12H and 12I a simple box cropping region centered on marker support structure tracking point 206 is shown.

These cropping masks may be used independently or in conjunction with one another at different stages of the registration process. For example, at an early stage of the registration process a large spherical region may be used to align multiple vertebral bodies in the surface data to volumetric images. In a second stage a cigar shaped cropping region may be used to refine the registration of the specific vertebral level. Finally, in a third stage a tight patient specific cropping mask generated from the preoperative CT scan of the particular level (through the use of registration support information) can be used to further refine the registration.

As mentioned before, the calibration of the surface imaging system to tracking system enables surface imaging based surgical guidance. However, the validity of the calibration transformation can be compromised, if the relative position between the tracking system and surfacing imaging system changed, for instance, due to physical impact.

In one example embodiment, the tracking marker support structure 45 is employed to compute a real-time calibration transformation between the tracking system and the surface imaging system, for example, to assess the validity of the previously determined calibration transformation. As described below, this can be achieved by performing surface detection to determine the position and orientation of the tracking marker support structure in the reference frame of the surface imaging system, and comparing this position with the position of the tracking marker support structure that is determined by the tracking system based on the detection of signals from the markers, where the comparison employs the last calibration transformation (the previously determined calibration transformation). The validity of the last calibration transformation can therefore be assessed by determining whether or not the computed position and orientation are within a prescribed tolerance.

This method may be performed at any time before or during a surgical procedure, such as at each time registration is performed, and optionally each time a tracking marker support structure is attached to a new skeletal feature of a patient. For example, in the case of a spinal surgical procedure, the method may be performed or repeated when the tracking marker support structure (or an additional tracking marker support structure) is attached to a new vertebral level.

Figure 13A:
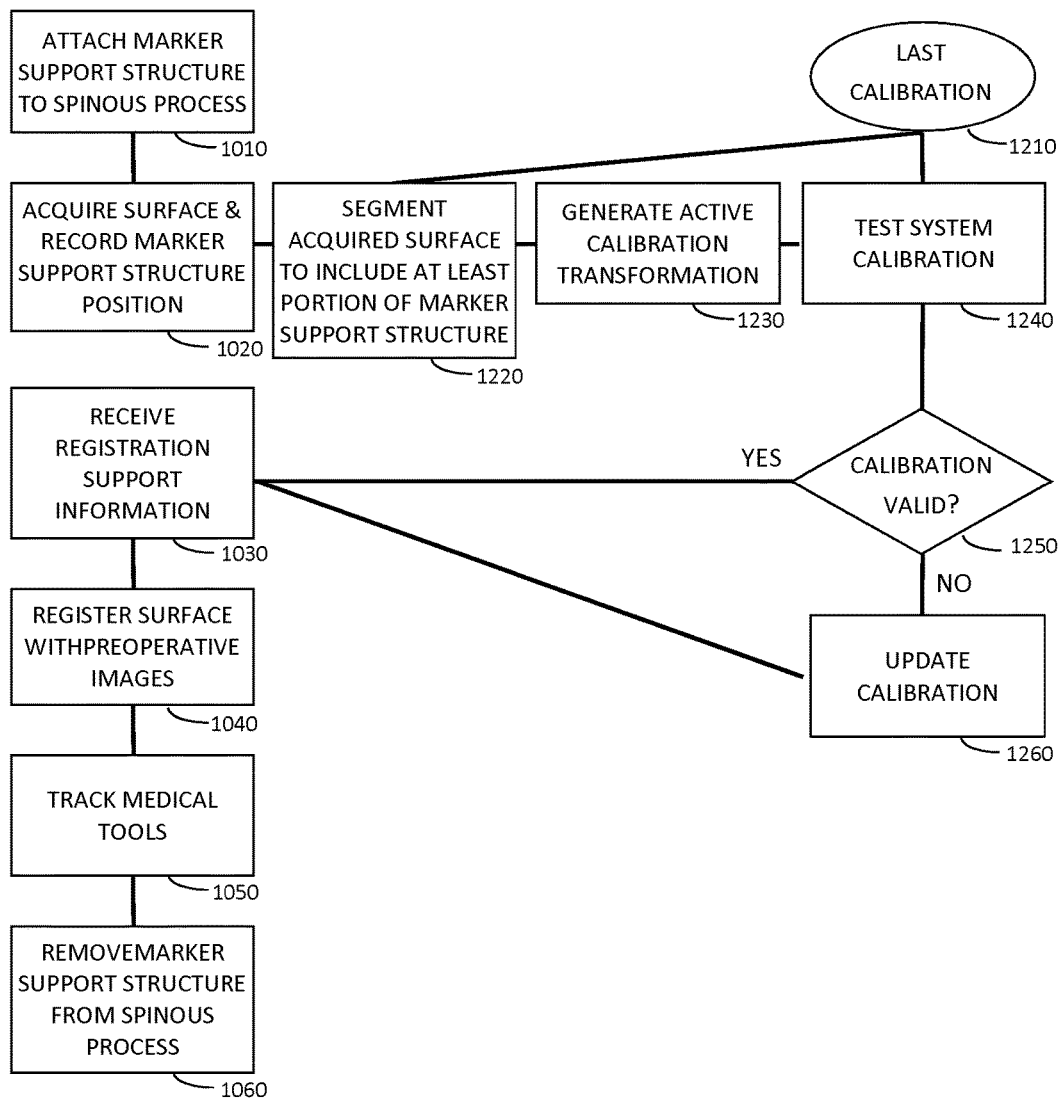
FIG. 13A illustrates an example method of employing a tracking marker support structure for the intraoperative assessment of the validity of a previously determined calibration transformation between a tracking system and a surface imaging system.

This method will be referred to herein as "active calibration" and an example process diagram is illustrated in FIG. 13A. The method includes some additional steps when compared to the process shown in FIG. 11 after attachment 1010 of the tracking marker support structure to the spinous process and acquisition of a surface of the surgical field 1020.

For active calibration, as shown in FIG. 13A, the acquired surface should include at least a portion of the tracking marker support structure 45, where the portion that is included has sufficient surface topology (i.e. includes one or more reference structures or surface features) to allow for the determination of the position and orientation of the tracking maker support structure via surface imaging. This is generally easily facilitated in the example case of a spinal surgical procedure because the tracking marker support structure 45 is typically directly attached to the vertebrae of interest.

Assuming that the previously determined calibration transformation is still sufficiently accurate, the transformation from the last calibration 1210 between the surface imaging system and tracking system can be used to identify a subregion within which to segment surface data associated with the tracking marker support structure from the acquired surface based on position tracked by the tracking system in step 1220.

Figure 13B:
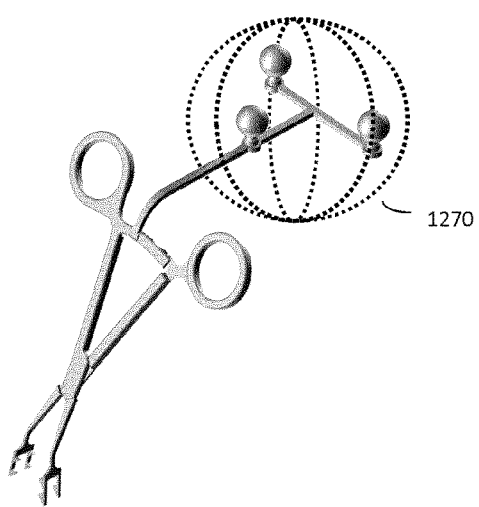
FIGS. 13B and 13C illustrate the use of cropping masks for the segmentation of a surface associated with the tracking marker support structure when performing active calibration.
Figure 13C:
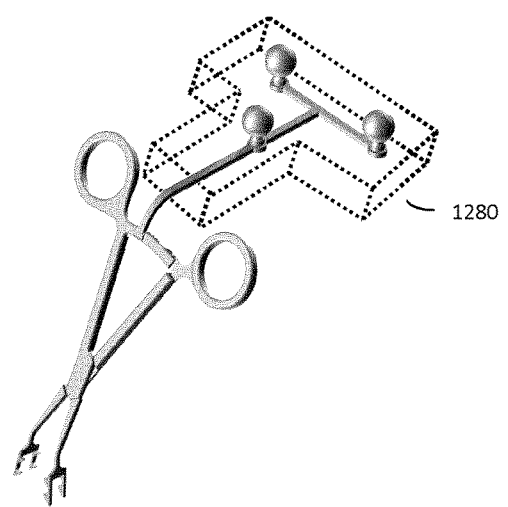

Since the tracking marker support structure is normally an isolated spatial structure, a simple cropping with a mask (e.g. a spherical mask) around the position predicted with the last calibration 1210 will likely be sufficient in step 1220. However, other cropping masks can be envisioned based on the known shape of the tracking marker support structure. FIGS. 13B and 13C depict examples of a spherical 1270 and a more conformal cropping mask 1280 for the marker support structure shown previously in FIGS. 3A and 3B.

Referring again to FIG. 13A, step 1230, the segmented tracking marker support structure from the acquired surface is registered to reference surface data characterizing the known surface of the tracking marker support structure (for example, a 3D-model of the tracking marker support structure or, for example, to a previously acquired surface of the tracking marker support structure) based on the position and orientation as currently measured by the tracking system, which yields in an active calibration transformation at the time of the surface acquisition 1020.

The active calibration is compared to the last calibration 1210 in step 1240 and 1250. If the active and the last calibration transformation lie within a specified tolerance, the last calibration transformation is deemed valid and may be used for the following registration (alternatively, the new calibration transformation may be used for future imaging registration). However, if the calibration transformations do not agree within the specific tolerance, the last calibration transformation is deemed invalid. The last calibration transformation may be automatically replaced with the active calibration transformation in step 1260 (alternatively, a new calibration transformation may be performed using a calibration reference device).

After this decision, the registration process continues at step 1030, in which registration support information is received, and at 1040 in which the acquired surface is registered with the volumetric images (either using the last calibration transformation—if valid—or with the updated active calibration transformation). The calibration transformation (last or newly updated) may then be used, as shown at 1050, for the tracking of surgical tools. After the surgical procedure is complete, or when a portion of the surgical procedure is complete (e.g. the portion pertaining to the position of the anatomical feature to which the tracking marker support structure is fixed, such as a given vertebral level) and the tracking marker support structure may be removed from the spinous process as shown at 1060.

It will be understood that steps 1230 and 1240 of FIG. 13A may be performed according to several different methods. For example, as described above, a new calibration transformation can be calculated (the active transformation), and compared to the last calibration transformation. In another example, the segmented surface data, registered to the reference surface data, can be used, with the last calibration transformation, to predict the current position of the tracking marker support structure, in the reference frame of the tracking system. This predicted position can be compared to the position that is currently measured by the tracking system. If the predicted and measured positions are within a prescribed tolerance, the last calibration transformation may be deemed to be valid. On the other hand, if the predicted and measured positions are outside of the prescribed tolerance, the last calibration transformation may be deemed to be invalid, and a new calibration transformation may be computed that results in the predicted position agreeing with the measured position. It will be understood that the comparisons between the positions may be made in the reference frame of the tracking system, or in the reference frame of the surface imaging system, according to variations of the aforementioned methods.

Figure 14A:
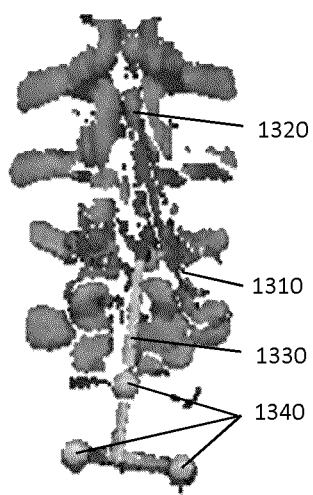
FIGS. 14A to 14E illustrate an active calibration process, in which a tracking marker support structure is employed to verify the calibration transformation between the tracking system and the surface imaging system.

FIGS. 14A-E show an example of the data outputs from the main steps of the process diagram illustrated in FIG. 13A. The surface image acquired in step 1020 is shown in FIG. 14A. The tracking marker support structure 1310 (showing some parts and the corresponding shadows) is attached to a spinous process 1320, which is going to be tracked after the registration. The tracking frame 1330 with the markers 1340 is clearly visible in the surface image and is used in this example for the active calibration.

Figure 14B:
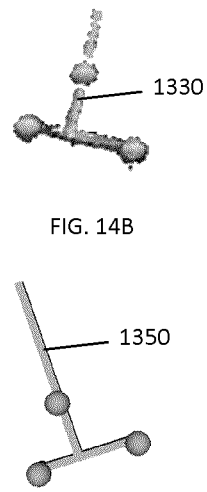
Figure 14C:
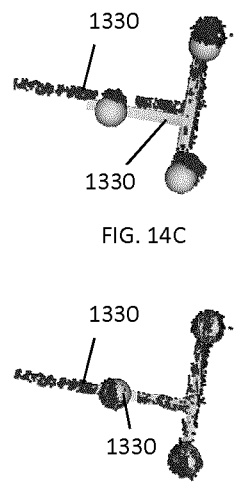
Figure 14D:
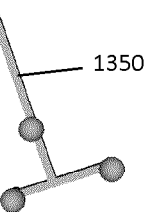
Figure 14E:
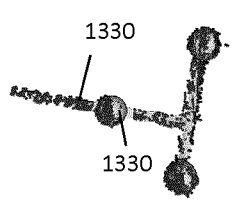

Using the marker positions acquired by the tracking system and the last calibration transformation, a spatial subregion is identified that is associated with the estimated position and orientation of the tracking marker support structure, such that at least a portion of the tracking marker support structure (in the present case, the tracking frame 1330) may be segmented in step 1220 from the surface image as shown in FIG. 14B. The known 3D-model 1350 of the tracking frame is shown in FIG. 14C. If the last calibration is invalid or corrupted, the calibration transformation of the 3D-model 1350 to the surface image 1330 of the tracking frame based on the tracking data results in a clear misalignment as shown in FIG. 14C. FIG. 14E shows the result after a registration of the data shown in FIG. 14D in step 1230. This yields in a new calibration transformation which may be employed, after the steps 1240 and 1250, as the active calibration transformation in step 1260.

In one example implementation of the aforementioned active calibration method, the system may provide a warning to the surgeon or system operator in step 1260 (see FIG. 13), if in the calibration test 1240 and 1250 the active and the last calibration transformation are not identical within a specified tolerance. For example, the user might be asked to provide input instruction whether the registration should be continued using the last calibration transformation, or using the active calibration, or even aborted.

Although the active calibration method is described above using a tracking marker support structure that is attached to an anatomical structure of the patient (e.g. a spinous process), it will be understood that in other example implementations, any other tool or tracking marker support structure with known 3D-desing can be used for active calibration, provided that the tool is tracked during the acquisition of the structural light and visible in the acquired surface.

In other example embodiments, the shape of the tracking frame (e.g. tracking frame 130 as shown in FIG. 2) can be designed so that the surface imaging system will always acquire a reference surface that is suitable (or optimal) for registration. For example, reference surfaces that may be incorporated into the shape of the tracking marker support structure include geometrical features such as pyramids, cubes, steps or chamfers, or other such features that ensure that the surface imaging system will acquire a surface from multiple possible views (i.e. relative positions between surface imaging system and tool).

Figure 15:
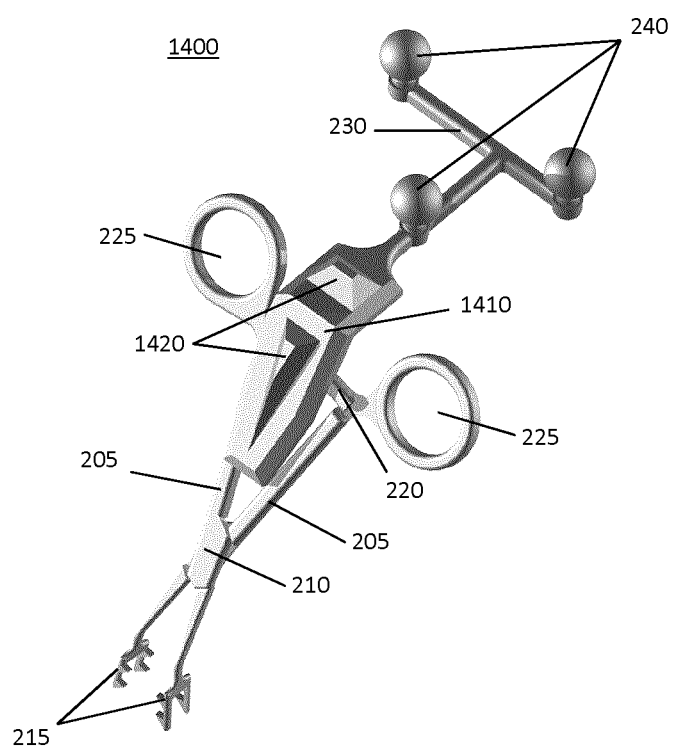
FIG. 15 illustrates an example implementation of a tracking marker support structure that incorporates an additional surface with characteristic structures that provide additional non-symmetric surfaces useful for the registration process.

For example, FIG. 15 illustrates an example implementation of a tracking marker support structure 1400 that incorporates an additional surface 1410 with characteristic structures 1420. These characteristic structures provide additional non-symmetric surfaces useful for the registration process. First, they enable the registration to be unique, whereas simple planar or spherical structures which have high degrees of symmetry may lead to registration ambiguity. Second, they reduce the probability of overexposure by the surface imaging system and/or ambient lighting conditions on all characteristic structures simultaneously. Furthermore, surface properties (roughness/reflectivity) of characteristic structures can also be tuned in order to optimize surface image acquisition based on surface imaging system specification and ambient environmental condition in which surface imaging system is meant to be used.

FIG. 16 itemizes characteristic features of the tracking marker support structure and provides a description as to how to select the parameter values for a given surgical application.

Figure 17:
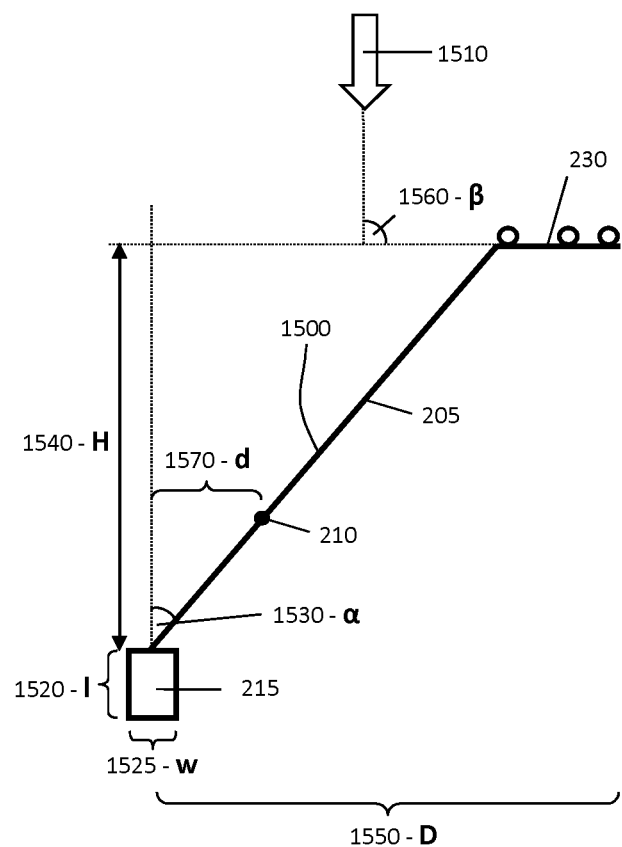
FIG. 17 shows a generalized profile of an example tracking marker support structure used for navigation of spinal procedures, identifying a set of characteristic geometrical parameters.

FIG. 17 shows a generalized profile 1500 of a tracking marker support structure used for navigation of spinal procedures. The profile includes the gripping jaws 215, the members 205, pin 210 connecting the members, and marker attachment 230. The arrow 1510 indicates the line-of-view of the combined tracking and a surface imaging system onto the tracking marker support structure during an example intended use with a patient lying in the prone position.

FIG. 17 defines identifies a set of characteristic geometrical parameters of the example tracking marker support structure. Example values for these dimensions for the example application of spinal surgical procedures are specified in FIG. 18.

Referring to FIG. 18, the length 1520 and width 1525 of the gripping tips 215 are given by the typical dimensions of a spinous process, to which the tracking marker support structure will be clamped. It can be advantageous to maximize the overlap of the clamping surface of the jaws with the spinous process in order to counteract the torque and to ensure stable attachment of the clamp to the spinous process. It will therefore be understood that a suitable size of the jaws 215 may depend on the anatomical regions of the spine (lumbar, thoracic and cervical) to which the device is to be attached. It will also be understand that the suitable size of the jaws may vary depending on the patient subgroups (for example pediatric vs. geriatric vs. healthy adult).

Referring again to FIG. 17, in order to avoid blocking of the line-of-sight 1510 of the surface imaging system onto the lateral laminae, the thickness of the gripping jaws should be as small as possible without compromising the mechanical integrity of the material. The angle 1530 subtended between normal direction 1540 and a longitudinal axis associated with members 210 should be greater than approximately 20° (e.g. between 20° and 40°), so that the tracking markers are not positioned directly above the surface of the spinous process.

It is also noted that pivot pin 210, which is located between members 205, could potentially block the line-of-sight onto the spinous process. Therefore, a minimal distance 1570 between pivot point 210 and to jaws 215 (along a longitudinal axis associated with members 205) can be beneficial, depending on the angle 1530 of the members 205. On the other hand, the necessary gripping force and mechanism as well as the spread of distal arms when releasing the clamping mechanism will define the position of the pivot pin 210.

As described above, the tracking marker support structure is intended to track the motion of the patient, as characterized by motion of the spinous process. Therefore, tracking marker support structure should not contact any other structures in the surgical cavity, which could transfer unwanted motion to the marker attachment 230. However, the marker attachment 230 requires a minimal profile size in order to achieve good tracking characteristics and might be close or even bigger than the profile of the surgical cavity. It is therefore advantageous that the marker attachment lie outside the surgical cavity when the tracking marker support structure is attached to the spinous process.

This can be achieved, for example, by positioning the marker attachment 230 such that marker attachment 230 resides at a perpendicular offset 1540 relative to of approximately 80 mm.

However, the overall size of the tracking marker support structure should be as small as possible to avoid blocking the surgeon's movement or the placement of other surgical instruments, such as, for example, a surgical microscope. Therefore, the perpendicular offset 1540 of the marker attachment relative to the gripping tip 1530 should not be above approximately 120 mm.

Another relevant issue is the potential for collision, shadowing or other interference between the tracking marker support structure and other tracked surgical instruments. Tracked surgical instruments commonly employ a set of fiducial markers that are positioned within a spatial region having a radius of approximately 40-70 mm relative to the shaft of the tracked instrument.

To avoid shadowing of such tracked tools by the marker attachment of the tracking marker support structure, the distance between marker attachment and jaws should be approximately 70 mm or more. This places the marker attachment at a distance that is sufficiently far from the surgical region of interest to result in spatial interference with tracked surgical tools. This distance also ensures that the marker attachment 230 of the tracking marker support structure will not obscure the line-of-sight for the surgeon or the structural light system 1510 onto the vertebra.

Because of the potential for the marker attachment, which may include addition surfaces 1410 and addition characteristic structures 1420, to weigh significantly more than the rest of the tracking marker support structure, a longer distance between marker attachment and the gripping jaws increases the torque applied about gripping jaws, which could damage the clamped tracking marker support structure or require a gripping force which might break the spinous process onto which it is being clamped.

As can be seen from FIG. 17, the horizontal distance D-1550 between marker attachment 230 and gripping jaws 215 and the distance H-1540 of the marker attachment 230 relative to the gripping tip 215 directly define the direction of the members 205 and therefore the angle α 1530 towards the gripping tip 215. The combined tracking and surface imaging system is normally positioned directly above the surgical cavity, which allows a direct line-of-sight 1510 with minimal shadowing effects. Since the marker attachment 230 should be perpendicular to optical axis 1510 to ensure optimal tracking, the angle of the marker attachment 1560 should be in the range between 70° and 110°.

Although the angles shown in the examples provided herein are shown as fixed angles, it will be understood that any or all angles may be replaced by adjustable angles having lockable joints which span the angular ranges specified or a subset of these ranges. Likewise, although the lengths of various components and members shown in the examples provided herein are shown being fixed, it will be understood that any or all lengths may be replaced by adjustable lengths (e.g. via telescopic members that are slidably engaged) having two or more lockable configurations that span the length ranges specified or a subset of these ranges.

In will be understood that any or all angles, which are shown as discontinuities in the profile in FIG. 17, may be replaced by smooth arcs or other shapes, which cover the same angular and distance range. For example, it will be understood that angles described and claimed herein may refer to the local angles at the point of attachment of one component to another, or to virtual angles associated with the intersection of the longitudinal axes associated with various components.

Other tracking marker support structures designs based on the feature set described in FIG. 16 can be generated for different anatomical locations. In fact, many of the realizations of tracking marker support structure shown in the examples provided herein can be employed in orthopedic shoulder surgery, where the tracking marker support structure is clamped to the spine of the scapula.

In other surgical applications, the tracking marker support structure could be configured, for example, according to FIG. 16 and based on the local anatomy.

Figure 19A:
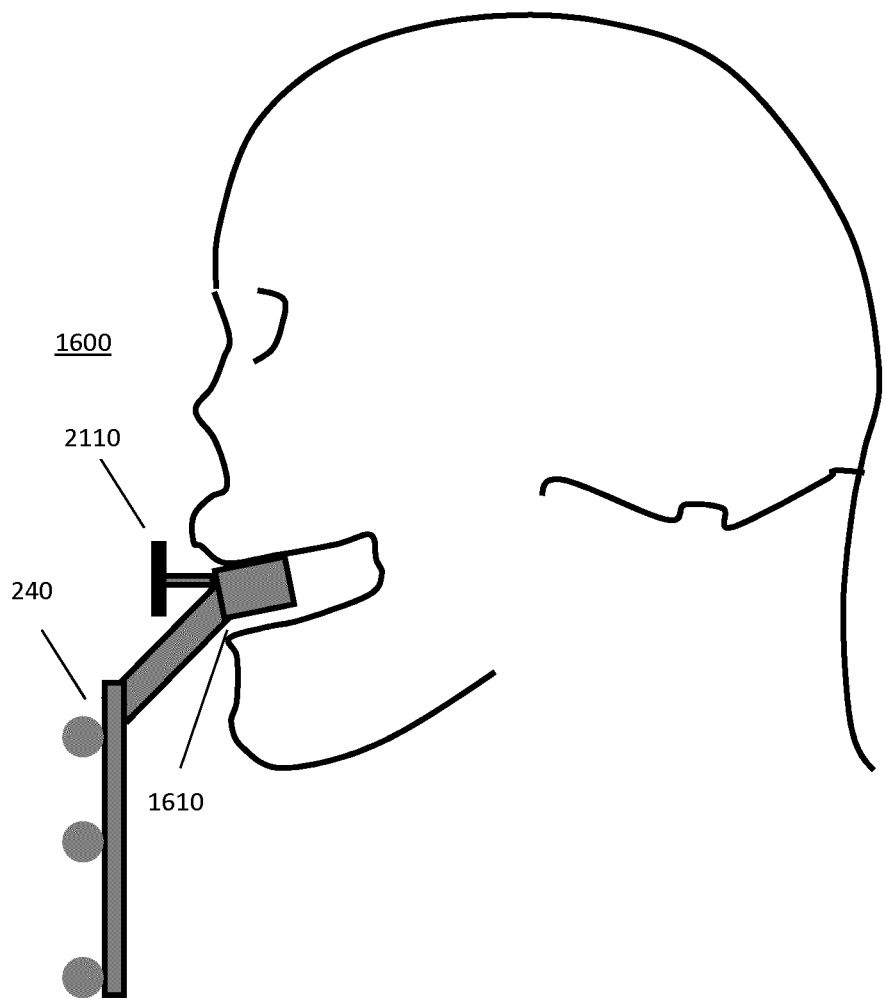
FIGS. 19A to 19D illustrate an example implementation of a tracking marker support structure based on the feature set shown in FIG. 16 and pertaining to cranial and/or maxillofacial surgical applications.
Figure 19B:
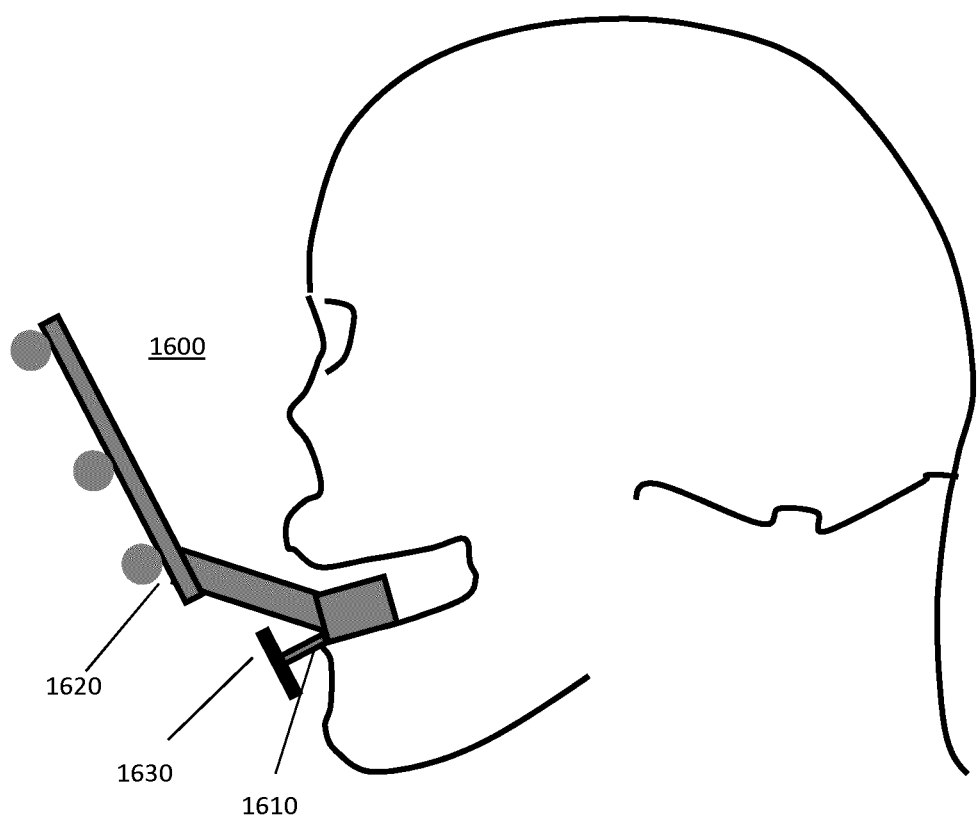
Figure 19C:
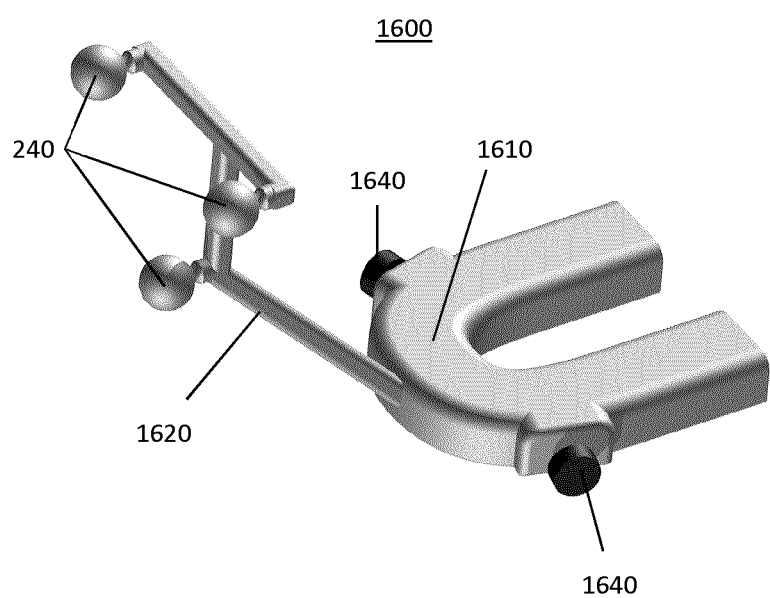
Figure 19D:
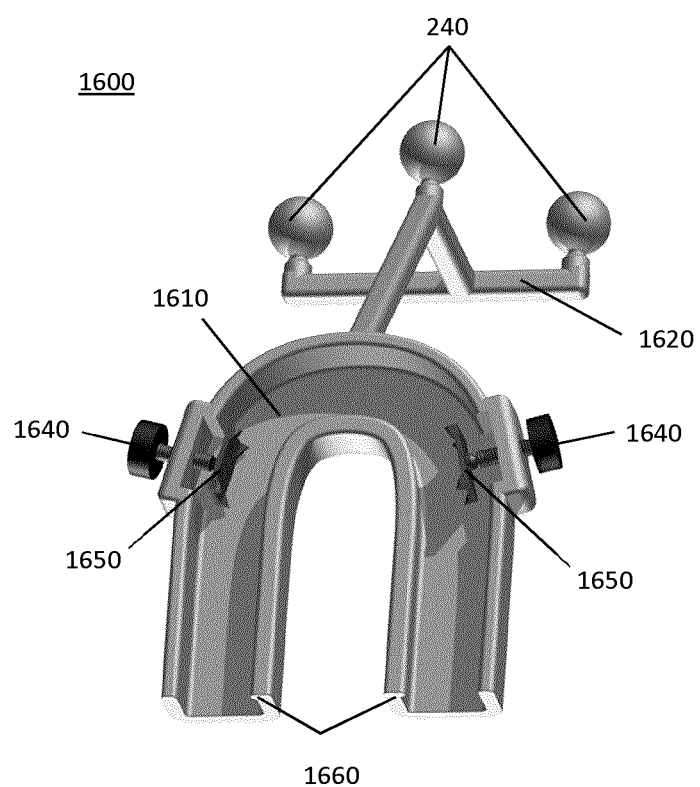

An example of a tracking marker support structure based on the feature set shown in FIG. 16 and pertaining to cranial and/or maxillofacial surgical applications is shown in FIG. 19A and FIG. 19B. In this example implementation, the tracking marker support structure 1600 comprises a mouth guard like portion 1610 which is clamped inside the mouth to either the upper (FIG. 19A) or lower (FIG. 19B) part of the jaw/teeth, depending on whether the lower member or the remainder of the skull is to be tracked. The tracking frame 1620 protrudes from the mouth such that it is visible to the navigation system and a screw based hinge mechanism 1630 is used to lock the clamp in place. A detailed view of the back and the front of the mouth guard and the screw based hinge mechanism is shown in FIG. 19C and FIG. 19D respectively. To connect the tracking marker support structure 1600, the mouth guard 1610 is pressed onto of the line of teeth. By tightening the two screws 1640 of the hinge mechanism 1630, the teeth is clamped between two fixation plates 1650 and the inner rim of the mouth guard 1660. Loosening the screws 1640, the marker support structure 1600 is removed from the teeth. This example provides another illustrative embodiment of a tracking marker support structure that is configured to attach to patient anatomy in a pre-selected orientation, which, as described above, may be useful in providing registration support information for use in performing registration of acquired surface data with volumetric image data.

Figure 19E:
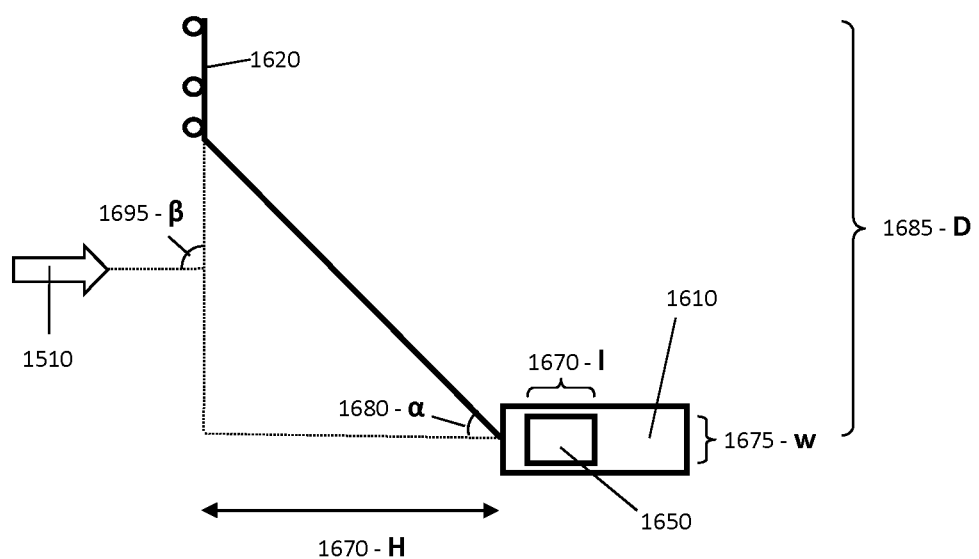
FIG. 19E shows a generalized profile of an example tracking marker support structure used for navigation of cranial and/or maxillofacial surgical procedures, identifying a set of characteristic geometrical parameters.
Figure 22A:
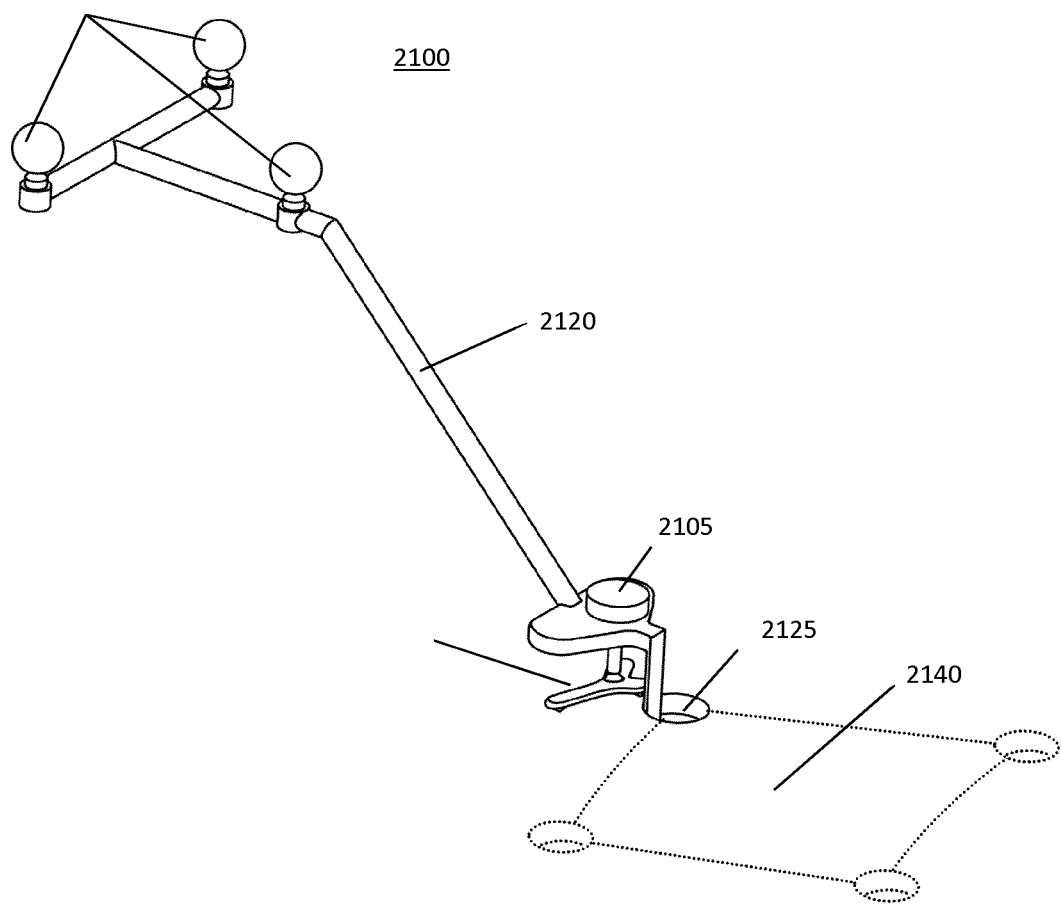
FIGS. 22A-22D illustrate an example implementation of a tracking marker support structure based on the feature set shown in FIG. 16 and pertaining to cranial based surgical procedures.
Figure 22B:
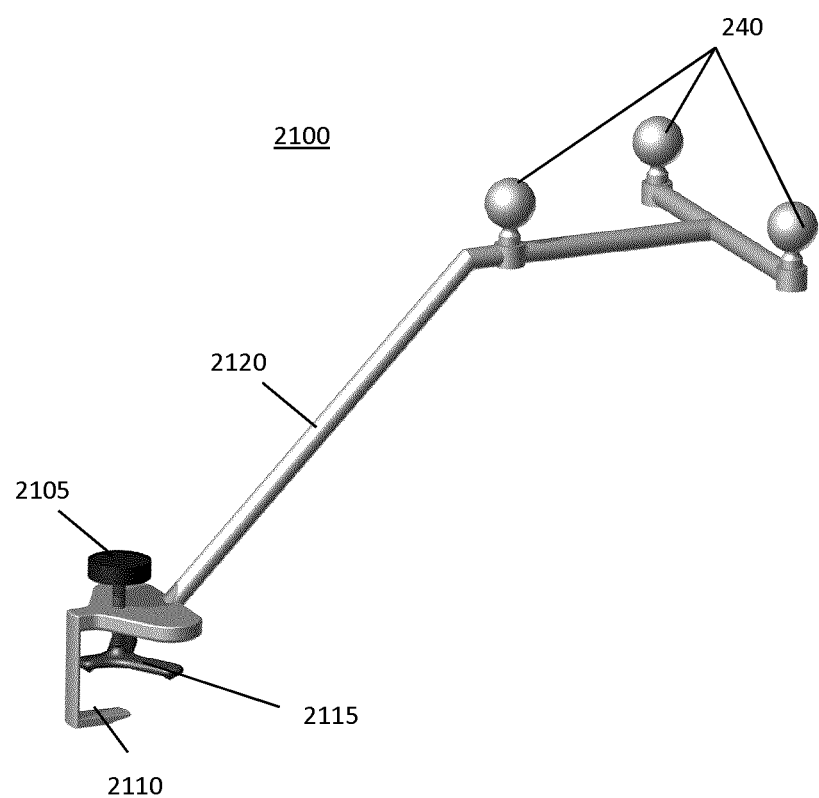
Figure 22C:
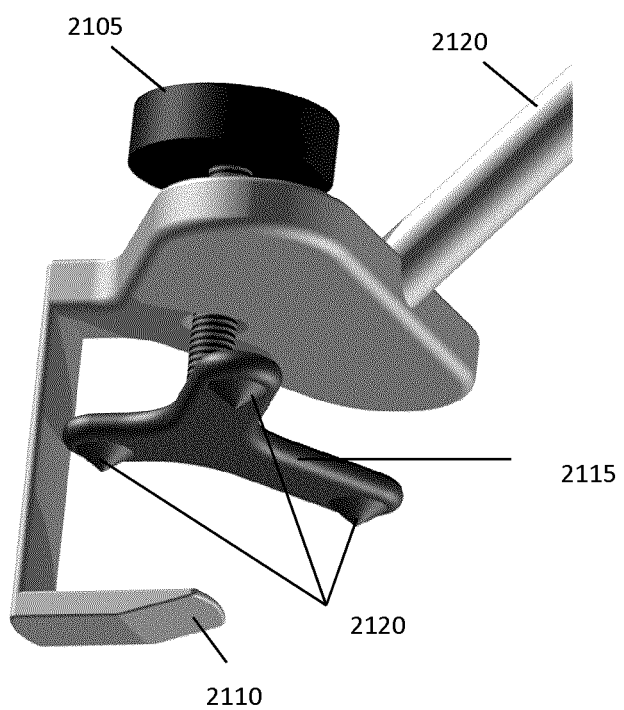
Figure 22D:
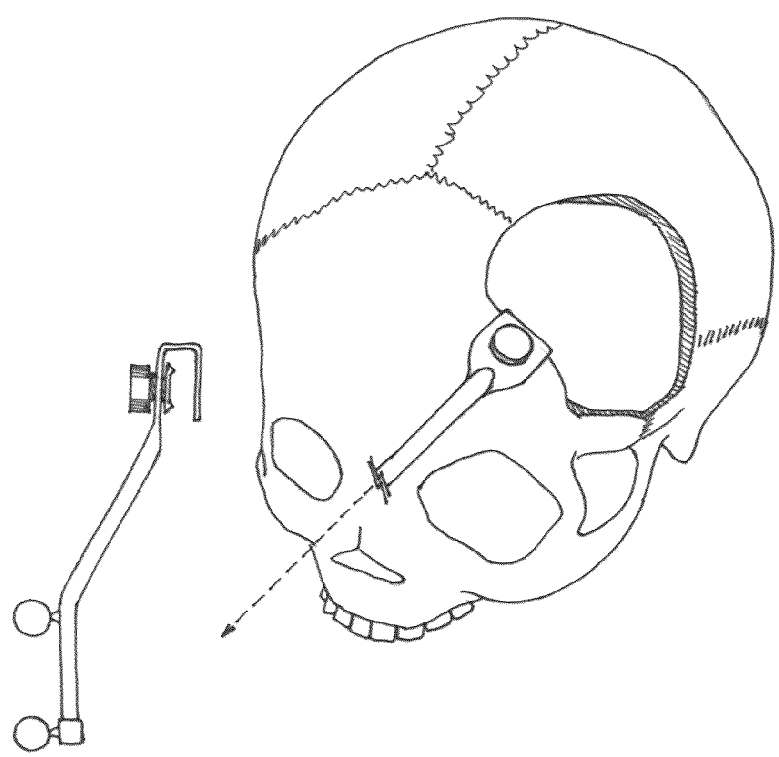
Figure 22E:
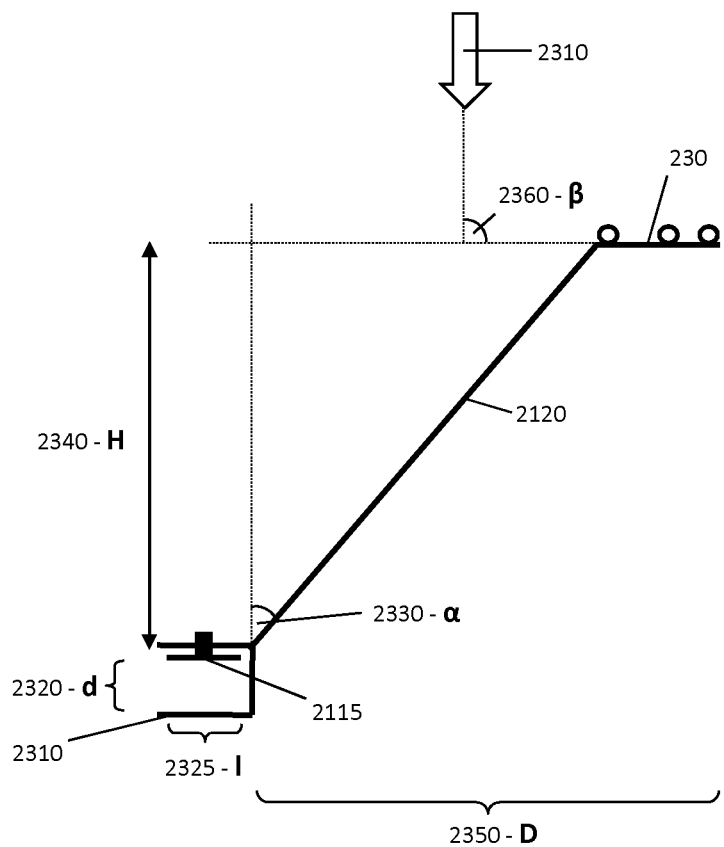
FIG. 22E shows a generalized profile of an example tracking marker support structure used for navigation of cranial based surgical procedures, identifying a set of characteristic geometrical parameters.

FIG. 19E shows a generalized profile of tracking marker support structure suitable for cranial and/or maxillofacial surgical applications. The profile's main features include marker attachment 1620 and clamping jaws 1650. The arrow 1510 indicates the line-of-view of the combined tracking and a surface imaging system onto the tracking marker support structure during an example intended use with a patient held in a stereotactic frame in a supine position. Much of the same motivation for features, dimensions and angles of generalized tracking marker support structure 1500, which is suitable for spine surgery and shown in FIG. 17, also directly carry over to this application. Examples values for dimensions and angles are shown in FIG. 19F. FIG. 22A-D shows an example of a tracking marker support structure 2100 for neurosurgical applications. The tracking marker support structure 2100 is used after the soft tissue has been retracted from the skull and one or more perforator holes have been made. The marker support structure hook 2110 is inserted into one of the perforator holes 2125 with hook 2110 positioned between the dura and the skull. During insertion the hook is positioned pointing away from the skull flap 2140 such that clamping is maintained after skull flap removal and good visualization of the cortical surface is maintained. The set screw 2105 is used to fix the tracking marker support structure into place using jaw 2120. Next registration to the skull surface is performed using the systems and methods described above. Finally the skull flap 2140 is removed and the navigated surgical procedure progresses in a standard fashion. Alternatively the surface of the brain or other internal structure could also be used for registration after skull flap 2140 has been removed. FIG. 22E shows a generalized profile of tracking marker support structure 2100 suitable for cranial procedures. Key features include jaw 2325 and marker attachment 230. Examples values for dimensions and angles for the generalized profile shown in FIG. 22E are shown in FIG. 22F. Dimensions for hook width is driven by the typical size of the perforator hole while the distance between the jaw and the hook is driven by typical skull thickness. Other distances ranges are specified primarily for not obstructing the line-of-sight of the tracking system and the surgeon's range of motion.

Figure 20:
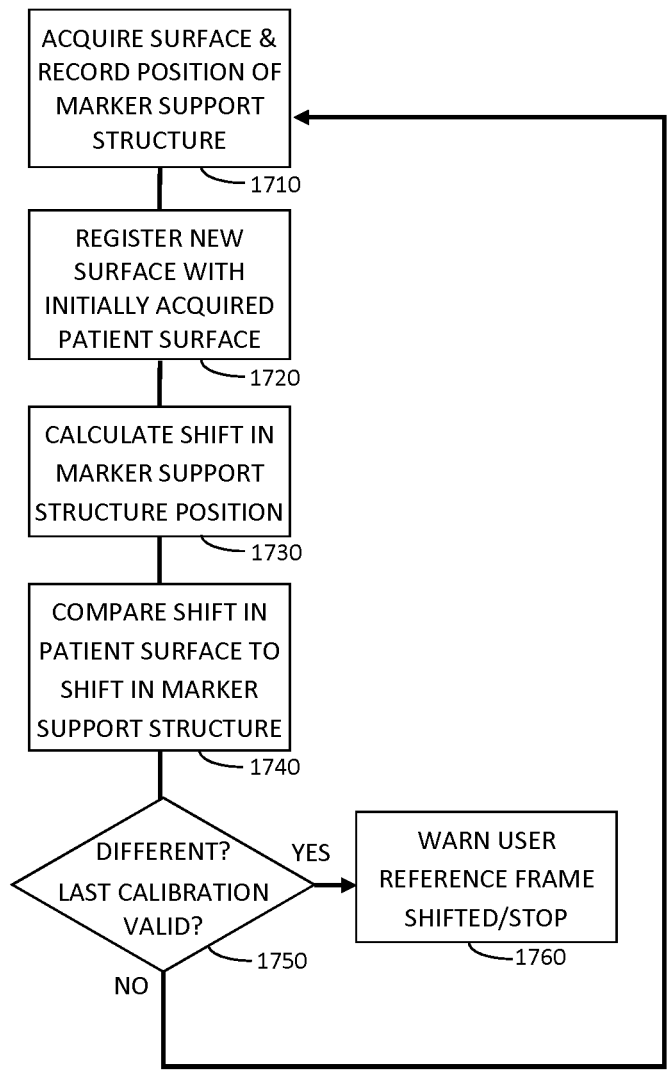
FIG. 20 shows a flow chart illustrating an example method in which a surface imaging based surgical guidance system is used to detect whether or not the tracking marker support structure has been bumped or moved intraoperatively from its initial position.

FIG. 20 shows a flow chart illustrating an example method in which a surface imaging based surgical guidance system is used to detect whether or not the tracking marker support structure has been bumped or moved intraoperatively from its initial position. The method involves intraoperatively reacquiring the surface data for the anatomical region of interest, and recording the current location of the tracking marker support structure as shown in step 1710. The new surface data is registered to the initially acquired surface data in step 1720, in order to obtain an intraoperative transformation within the reference frame of the surface imaging system. The intraoperative transformation is then employed to estimate the current position and orientation of the tracking marker support structure in the reference frame of the tracking system, based on the previously known position of the tracking marker support structure, as shown at step 1730. If there has been little or no movement of the tracking marker support structure position relative to the patient, then the transformations describing the tracking marker support structure motion and patient surface motion between the two time points will lie within a pre-selected threshold. In other words, the intraoperative transformation can be compared to the difference between the current and previous position and orientation of the tracking marker support structure, in order to detect a change in the position and orientation of the tracking marker support structure relative to the patient.

This check is performed in step 1740 with the output 1750 either triggering a warning (e.g. alerting a user of the system) and potentially stopping tracking 1760, if the transformations are significantly different or allowing the tracking to continue if the change in the relative position and orientation of the tracking marker support structure lies within a pre-selected tolerance. This procedure can be performed at any time after initial attachment of the tracking marker support structure to the patient anatomy. For example, the method may be performed at a pre-selected frequency, or, for example, on demand as initiated by the surgeon or operator, or for example, each time a new step in the surgical plan is to be executed.

It will be understood that the verification procedure described above and shown in FIG. 20 is equally valid if the surface imaging subsystem is used to measure the new position of the tracking marker support structure (for comparison with the estimated position). It is also to be understood that the active calibration procedure described in FIG. 13 can also be applied in combination with the verification method in order to simultaneously mitigate effects of relative motion between the surface imaging subsystem and tracking subsystem.

In another embodiment, a method of data segmentation pertaining to surface imaging surgical guidance system is presented. In some applications, it may be advantageous to remove surface data pertaining to instruments tracked by the tracking system from the surface data acquired by the surface imaging subsystem. This can be accomplished, for example, by using a known shape or geometry (e.g. as provided by CAD/engineering design files or a known 3D model) of tools being tracked by the tracking subsystem.

In one example implementation, the method involves intraoperatively acquiring the surface data using a surface imaging system, the surface data including surface artifacts associated with the surface of an instrument, detecting, with a tracking system, signals associated with the fiducial markers located on the instrument, and processing the signals to determine an intraoperative position and orientation of the instrument. The intraoperative position and orientation of the instrument may then be used, along with the calibration transformation between the reference frames associated with the tracking system and the surface imaging system, to determine a suitable position and orientation of a cropping mask for removal of the surface artifacts associated with the instrument. The cropping mask, correctly positioned relative to the surface data (e.g. where the cropping mask has been transformed into the reference frame of the surface imaging device), may then be employed to segment the surface data to remove the surface artifacts within the region associated with the cropping mask.

Figure 21:
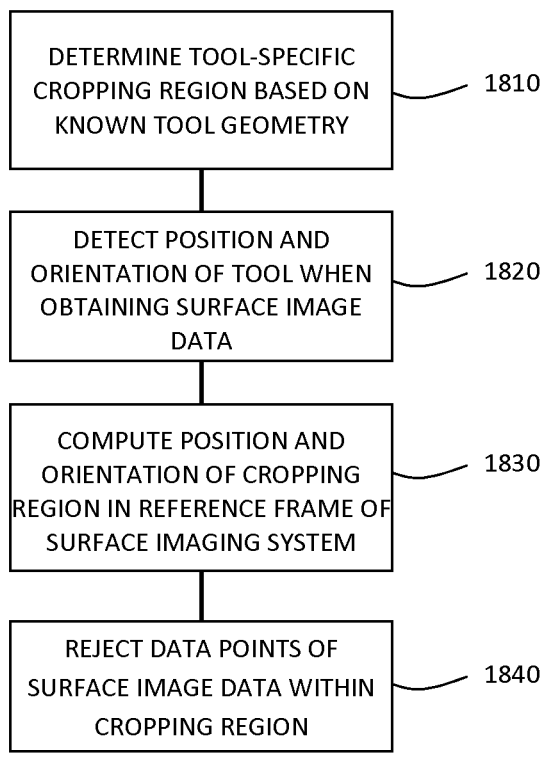
FIG. 21 is a flow chart illustrating such an example method of performing selective surface segmentation based on known properties of tools or instruments that may be present within the field of view of a surface imaging system.

FIG. 21 is a flow chart illustrating such an example method of performing selective surface segmentation based on known properties of tools or instruments that may be present within the field of view of a surface imaging system. First, in step 1810, a tool-specific cropping region is generated based on the known geometrical properties of the tool CAD file. As shown at step 1820, the tool position and orientation is determined (e.g. measured with the tracking system) when surface data of the anatomical region is acquired. The cropping region is positioned and oriented based on the detected position and orientation of the tool, as determined based on data acquired from the tracking subsystem. This cropping region may be initially specified within the frame of reference of the tracking subsystem, and then shifted into the coordinate system of the surface imaging subsystem using the transformation linking the two subsystems, as shown at step 1830. Alternatively, the position and orientation of the tool within the reference frame of the surface imaging system, and the cropping region may be generated within the reference frame of the surface imaging system. The cropping region is then used to reject points within the acquired surface data that lie within the cropping region, as shown at step 1840. This method, or variations thereof, may be employed to improve the quality and robustness of the registration process between surfaced data and volumetric image data and/or surface data acquired at two or more time points (where surgical tools may be in two different locations).

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of assessing the validity of a previously determined calibration transformation between a reference frame of a surface imaging system and a reference frame of a tracking system, the method comprising:
    obtaining reference surface data characterizing a surface profile of a tracking marker support structure;
    detecting, with the tracking system, signals associated with fiducial markers located on the tracking marker support structure, wherein the tracking marker support structure is removably attached to a patient during a medical procedure;
    acquiring surface data using the surface imaging system, wherein the surface data is obtained from a spatial region that includes at least a portion of the tracking marker support structure;
    processing the signals to calculate the position and orientation of the tracking marker support structure in the reference frame of the tracking system;
    processing the surface data and the reference surface data to calculate the position and orientation of the tracking marker support structure in the reference frame of the surface imaging system;
    employing the position and orientation of the tracking marker support structure in the reference frame of the surface imaging system and the position and orientation of the tracking marker support structure in the reference frame of the tracking system, and the previously determined calibration transformation to provide comparative measures for assessing the validity of the previously determined calibration transformation; and
    processing the comparative measures to assess the validity of the previously determined calibration transformation.

2. The method according to claim 1 wherein the tracking marker support structure comprises one or more characteristic structures suitable for performing surface registration when processing the surface data and the reference surface data.

3. The method according to claim 2 wherein at least one characteristic structure comprises a plurality of surfaces respectively oriented at oblique angles.

4. The method according to claim 2 wherein the characteristic structures are non-spherical.

5. The method according to claim 1 wherein the validity of the previously determined calibration transformation is assessed by:
    computing a current calibration transform for the position and orientation of the tracking marker support structure between the reference frame of the surface imaging system and the reference frame of the tracking marker support structure; and
    comparing the current calibration transform to the previously determined calibration transformation.

6. The method according to claim 1 wherein the validity of the previously determined calibration transformation is assessed by:
    employing the previously determined calibration transformation to determine, based on the calculated position and orientation of the tracking marker support structure in the reference frame of the surface imaging system, an estimated position and orientation of the tracking marker support structure in the reference frame of the tracking system; and
    comparing the estimated position and orientation of the tracking marker support structure in the reference frame of the tracking system to the calculated position and orientation of the tracking marker support structure in the reference frame of the tracking system.

7. The method according to claim 1 wherein the validity of the previously determined calibration transformation is assessed by:
    employing the previously determined calibration transformation to determine, based on the calculated position and orientation of the tracking marker support structure in the reference frame of the tracking system, an estimated position and orientation of the tracking marker support structure in the reference frame of the surface imaging system; and
    comparing the estimated position and orientation of the tracking marker support structure in the reference frame of the surface imaging system to the calculated position and orientation of the tracking marker support structure in the reference frame of the surface imaging system.

8. The method according to claim 1 wherein the reference surface data is obtained from a three-dimensional model of at least a portion of the tracking marker support structure.

9. The method according to claim 1 wherein the reference surface data comprises previously measured surface data.

10. The method according to claim 1 wherein processing the surface data to determine the position and orientation of the tracking marker support structure in the reference frame of the surface imaging system comprises:

processing the position and orientation of the tracking marker support structure in the reference frame of the tracking system and the previously determined calibration transformation to determine an estimated position and orientation of the tracking marker support structure in the reference frame of the surface imaging system;

segmenting the surface data within a spatial subregion associated with the estimated position and orientation of the tracking marker support structure to obtain a segmented surface associated with the tracking marker support structure; and registering the segmented surface to the reference surface data.

11. The method according to claim 10 wherein the tracking marker support structure comprises one or more characteristic structures suitable for performing surface registration when processing the surface data and the reference surface data, and wherein the spatial subregion is selected to include the one or more characteristic structures.

12. The method according to claim 11 wherein at least one characteristic structure comprises a plurality of surfaces respectively oriented at oblique angles.

13. The method according to claim 11 wherein the one or more characteristic structures are non-spherical.

14. The method according to claim 10 wherein the spatial subregion is prescribed by a pre-selected mask.

15. The method according to claim 14 wherein the pre-selected mask is associated with a shape of the tracking marker support structure.

16. The method according to claim 14 wherein the pre-selected mask is a conformal mask that conforms to a shape of the tracking marker support structure.

17. The method according to claim 10 wherein the reference surface data is obtained from a three-dimensional model of at least a portion of the tracking marker support structure.

18. The method according to claim 10 wherein the reference surface data comprises previously measured surface data.

19. The method according to claim 1 further comprising employing the calculated positions and orientations of the tracking marker support structure to generate a new calibration transformation between the reference frame of the surface imaging system and the reference frame of the tracking system.

20. The method according to claim 19 further comprising replacing the previously determined calibration transformation with the new calibration transformation.

21. The method according to claim 19 replacing the previously determined calibration transformation with the new calibration transformation when the previously determined calibration transformation is found to be invalid.

22. The method according to claim 1 wherein the validity of the previously determined calibration transformation is assessed intraoperatively.

23. The method according to claim 1 wherein the validity of the previously determined calibration transformation is assessed in real-time.

24. The method according to claim 1 wherein the medical procedure is a spinal medical procedure, and wherein the validity of the previously determined calibration transformation assessed when the tracking marker support structure is attached to a vertebral level.

* * * * *